US007825136B2

(12) United States Patent
Grossman

(10) Patent No.: US 7,825,136 B2
(45) Date of Patent: Nov. 2, 2010

(54) POTENTIATORS OF ANTIBACTERIAL ACTIVITY

(75) Inventor: Trudy Hope Grossman, Lexington, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1432 days.

(21) Appl. No.: 10/887,719

(22) Filed: Jul. 9, 2004

(65) Prior Publication Data

US 2005/0090482 A1 Apr. 28, 2005

Related U.S. Application Data

(60) Provisional application No. 60/486,041, filed on Jul. 10, 2003, provisional application No. 60/486,046, filed on Jul. 10, 2003, provisional application No. 60/486,102, filed on Jul. 10, 2003, provisional application No. 60/486,235, filed on Jul. 10, 2003.

(51) Int. Cl.
| | |
|---|---|
| *A01N 43/40* | (2006.01) |
| *A01N 43/04* | (2006.01) |
| *A61K 31/445* | (2006.01) |
| *A61K 31/497* | (2006.01) |
| *A61K 31/4965* | (2006.01) |
| *A61K 31/70* | (2006.01) |

(52) U.S. Cl. ............... 514/318; 514/37; 514/254.01; 514/255.01

(58) Field of Classification Search ............... 514/318
See application file for complete search history.

(56) References Cited

U.S. PATENT DOCUMENTS 4,853,225 A * 8/1989 Wahlig et al. ............ 424/423
5,260,066 A * 11/1993 Wood et al. ............. 424/447
5,543,423 A    8/1996 Zelle et al. .............. 514/332
5,620,971 A    4/1997 Armistead et al. ........ 514/212
5,989,832 A   11/1999 Trias et al. .............. 435/7.2
6,436,980 B1   8/2002 Leger et al. ............. 514/375
6,982,091 B2 * 1/2006 Pauletti et al. ........... 424/430
7,189,740 B2 * 3/2007 Zeldis .................... 514/323

FOREIGN PATENT DOCUMENTS

WO    WO 96/36630    11/1996
WO    WO 97/36869    10/1997

OTHER PUBLICATIONS

RD269008A, Sep. 1986, Anonymous.*
W. N. Konings and G. J. Poelarends, "Bacterial Multidrug Resistance Mediated by a Homologue of the Human Multidrug Transporter P-glycoprotein", *IUBMB Life*, 53: 213-218 (2002).
H. W. Van Veen, et al., "Multidrug Resistance Mediated by a Bacterial Homolog of the Human Multidrug Transporter MDR1" *Proc. Natl. Acad. Sci. USA*, 93: 10668-10672 (1996).
Database Medline 'Online! US National Library of Medicine (NLM), Bethesda, MD, US; Database Accession No. NLM15504837; XP002304037; S. Mullin et al., "Inhibition of Antibiotic Efflux in Bacteria by the Novel Multidrug Resistance Inhibitors Biricodar (VX-710) and Timcodar (VX-853)", *Antimicrobial Agents and Chemotherapy*, 48:4171-4176 (2004). (abstract only).
On Line Medical Dictionary, 'Online! May 6, 1997; Retrieved from the Internet URL:http://cancerweb.ncl.ac.uk/cgi-bin/omd?query=actinomycin+d>, retrieved on Nov. 11, 2004; XP002304031.

* cited by examiner

*Primary Examiner*—Sreeni Padmanabhan
*Assistant Examiner*—Layla Soroush
(74) *Attorney, Agent, or Firm*—Michael J. DiVerdi

(57) ABSTRACT

The present invention relates to compounds that potentiate the activity of antibacterials. The present invention also relates to compositions useful in treating bacterial infection in mammals, and methods therewith. The present invention also relates to a method of inhibiting bacterial efflux of an antibiotic, thereby increasing the efficacy of the antibiotic.

5 Claims, 1 Drawing Sheet

POTENTIATORS OF ANTIBACTERIAL ACTIVITY

This application claims benefit of U.S. provisional applications Nos. 60/486,046, 60/486,235, 60/486,102, 60/486,041, all filed Jul. 10, 2003, the disclosures of which are incorporated by reference.

TECHNICAL FIELD OF THE INVENTION

The present invention relates to compounds that potentiate the activity of antibacterials. The present invention also relates to compositions useful in treating bacterial infection in mammals, and methods therewith. The present invention also relates to a method of inhibiting bacterial efflux of an antibiotic, thereby increasing the efficacy of the antibiotic.

BACKGROUND OF THE INVENTION

Bacteria can become resistant to antibiotics via three main mechanisms: antibiotic inactivation, target modification and alteration of intracellular antibiotic concentration. The latter mechanism can occur by either decreasing permeability to an antibiotic or by increasing the activities of a variety of efflux pumps. While permeability is a significant barrier to antibiotics in gram-negative bacteria, due to the presence of an outer membrane, it is an unlikely mechanism of resistance for gram-positive bacteria that lack an outer membrane. Both gram-positive and gram-negative bacteria possess multiple, chromosomal- and plasmid-encoded efflux pumps with broad substrate specificities. Putnam et al., "Molecular properties of bacterial multidrug transporters," Microbiol. and Molecular Biol. Rev., 64:672-693 (2000); Munoz-Bellido et al., "Efflux-mediated antibiotic resistance in Gram positive bacteria," Reviews. Med. Microbiol., 13:1-13 (2002); Bambeke et al., "Antibiotic efflux pumps," Biochem. Pharmacol., 60:457-470 (2000).

One natural role of efflux pumps in prokaryotic and eukaryotic cells is to remove toxins from the interior of the cell. This protective function enables bacterial cells to survive in hostile environments, including the presence of antibiotics during the treatment of infections. Efflux of antibiotics is a clinically significant general resistance mechanism for bacteria. Kohler et al., "Bacterial antibiotic efflux systems of medical importance," Cell. Mol. Life Sci., 56:771-778 (1999). The up-regulation of efflux systems through physiological induction and spontaneous mutation can significantly lower the intracellular concentration of many antibiotics, causing an impact on clinical efficacy. Bacteria can express multiple efflux pumps which are capable of extruding a wide variety of structurally unrelated compounds, including both naturally and synthetically produced antibiotics. For instance, the sequence of the *S. aureus* genome indicates that this organism may possess up to 17 drug transporters or more since an analysis of the genome sequence of methicillin-resistant *Staphylococcus aureus* N315 indicates that there are >20 open reading frames capable of encoding antibiotic efflux pumps. Kuroda et al., "Whole genome sequencing of methicillin-resistant *Staphylococcus aureus*," Lancet, 357:1225-1240 (2001) and http://www.membranetransport.org.

For gram-negative bacteria, the resistance-nodulation-cell division (RND) family of pumps play the greatest role in contributing to resistance to clinically relevant antibiotics. Examples of this class of efflux pumps include the AcrB pump in *E. coli* and the MexB, D, F and Y pumps in *P. aeruginosa* (Bambeke et al., "Antibiotic efflux pumps", Biochem. Pharmacol. 60:457-470 (2000) and Putman, van Veen and Konings, "Molecular properties of bacterial multidrug transporters", Microbiol. Mol. Biol. Rev. 64:672-693 (2000)).

To date, RND pumps have not been described in gram-positive organisms. For gram-positive bacteria, the major facilitator superfamily class (MFS) pumps play the greater role in the efflux of clinically relevant antibiotics, contributing to clinical resistance. MFS pumps have been found in both prokaryotes and eukaryotes, including mammals, and examples of this class of efflux pumps include the NorA pump in *S. aureus* (Neyfakh et al., "Fluoroquinolone resistance protein NorA of *Staphylococcus aureus* is a multidrug efflux transporter", Antimicrob. Agents Chemother. 37:128-129 (1993)), the PmrA pump in *S. pneumoniae* (Gill et al., "Identification of an efflux pump gene, pmrA, associated with fluoroquinolone resistance in *Streptococcus pneumoniae*," Antimicrob. Agents Chemother., 43:187-189 (1999)), and the EmeA pump of *E. faecalis* (Lee et al., "Functional cloning and expression of emeA, and characterization of EmeA, a multidrug efflux pump from *Enterococcus faecalis*," Biol. Pharm. Bull., 26:266-270 (2003)).

Recent reports have described the crystal structures of the *E. coli* AcrB pump (Murakami et al., "Crystal structure of bacterial multidrug efflux transporter AcrB", Nature 419: 587-593 (2002) and Yu et al., "Structural basis of multiple drug-binding capacity of the AcrB multidrug efflux pump", Science 300:976-980 (2003)) and the *Bacillus subtilis* BmrR MDR transcriptional activator (Zheleznova et al., "Structural basis of multidrug recognition by BmrR, a transcription activator of a multidrug transporter", Cell 96:353-362 (1999)), both co-complexed with substrates, and the outer membrane transporter TolC (Koronakis et al., "Crystal structure of the bacterial membrane protein TolC central to multidrug efflux and protein export", Nature 405:914-919 (2000)). While structural details provide the basis for substrate recognition, the mechanism by which molecules are actually transported to the outside of a cell remains to be elucidated. In addition, while there is some degree of substrate overlap between RND- and MFS-type pumps, there are sufficient differences in their substrate specificities and structures to explain that several known pump inhibitors only inhibit one family or the other, but not both.

Inhibition of efflux is one way to increase the clinical efficacy of an antibiotic even in the presence of target-based mutations. In response to emerging resistance to all classes of antibiotics, in particular fluoroquinolones, this has been a significant focus of the pharmaceutical industry (Lawrence and Barrett, "Inhibition of bacterial efflux: needs, opportunities, and strategies," Curr. Opin. Antiinfect. Invest. Drugs, 2:145-153 (2000)). Many pharmaceutical industry programs have focused on identifying inhibitors of gram-negative and gram-positive efflux systems that could potentially be used in combination with antibiotics to improve their efficacy and suppress resistance (Aeschlimann et al., "Effects of NorA inhibitors on in vitro antibacterial activities and postantibiotic effects of levofloxacin, ciprofloxacin, and norfloxacin in genetically related strains of *Staphylococcus aureus*", Antimicrob. Agents Chemother. 43:335-340 (1999); Bambeke et al., "Antibiotic efflux pumps", Biochem. Pharmacol. 60:457-470 (2000); Germann et al., "Cellular and biochemical characterization of VX-710 as a chemosensitizer: reversal of P-glyco-protein-mediated multidrug resistance in vitro", Anticancer Drugs 8:125-140 (1997); Kaatz et al., "Identification and characterization of a novel efflux-related multidrug resistance phenotype in *Staphylococcus aureus*", J. Antimicrob. Chemother. 50:833-838 (2002); Kuroda et al., "Whole genome sequencing of methicillin-resistant *Staphy-* lococcus aureus", Lancet 357:1225-1240 (2001); Lee et al., "Functional cloning and expression of emeA, and characterization of EmeA, a multidrug efflux pump from *Enterococcus faecalis*", Biol. Pharm. Bull. 26:266-270 (2003); Markham et al., "Inhibition of the multidrug transporter NorA prevents emergence of norfloxacin resistance in *Staphylococcus aureus*", Antimicrob. Agents Chemother. 40:2673-2674 (1996); Putman et al., "Molecular properties of bacterial multidrug transporters", Microbiol. Mol. Biol. Rev. 64:672-693 (2000); Renau et al., "Conformationally-restricted analogues of efflux pump inhibitors that potentiate the activity of levofloxacin in *Pseudomonas aeruginosa*", Bioorg. Med. Chem. Lett. 13:2755-2758 (2003); Rowinsky et al., "Phase I and pharmacokinetic study of paclitaxel in combination with biricodar, a novel agent that reverses multidrug resistance conferred by overexpression of both MDR1 and MRP", J. Clin. Oncol. 16:2964-2976 (1998)).

In vitro, efflux pump inhibitors (EPIs) have been shown to reduce spontaneous resistance frequencies of antibiotics in *P. aeruginosa* (Lomovskaya et al., "Identification and characterization of inhibitors of multidrug resistance efflux pumps in *Pseudomonas aeruginosa*: novel agents for combination therapy", Antimicrob. Agents Chemother. 45:105-116 (2001)), *S. pneumoniae* (Markham et al., "Inhibition of the emergence of ciprofloxacin resistance in *Streptococcus pneumoniae* by the multidrug efflux inhibitor reserpine", Antimicrob. Agents Chemother. 43:988-989 (1999)), and *S. aureus* (Markham et al., "Inhibition of the multidrug transporter NorA prevents emergence of norfloxacin resistance in *Staphylococcus aureus*", Antimicrob. Agents Chemother. 40:2673-2674 (1996); Markham et al., "Multiple Novel Inhibitors of the NorA Multidrug Transporter of *Staphylococcus aureus*", Antimicrob. Agents Chemother. 43:2404-2408 (1999)). In an animal model of *P. aeruginosa* infection, Renau, et al., "Inhibitors of efflux pumps in *Pseudomonas aeruginosa* potentiate the activity of the fluoroquinolone levofloxacin", J. Med. Chem. 42:4928-4931 (1999)) showed that levofloxacin plus an EPI was more efficacious than levofloxacin alone, demonstrating the potential for combination therapy in vivo.

Reserpine, a plant alkaloid, is a known inhibitor of both mammalian and gram-positive bacterial efflux whose clinical utility is limited by neurotoxicity (Neyfakh, et al., "Efflux-mediated multidrug resistance in *Bacillus subtilis*: Similarities and dissimilarities with the mammalian system," Proc. Nat'l Acad. Sci., 88:4781-4785 (1991)). Reserpine has activity against the MFS *S. aureus* NorA pump, a well-known contributor to fluoroquinolone resistance in this organism. Homologs of the NorA pump can be found in multiple gram-positive bacteria suggesting that reserpine, and other NorA pump inhibitors, would work with other clinical pathogens.

Thus, there is a need for compounds that potentiate the activity of an antibacterial (e.g., an antibiotic). There is also a need for compositions useful in treating bacterial infection in mammals, and methods therewith. There is also a need for a method of inhibiting bacterial efflux of an antibiotic, thereby increasing the efficacy of the antibiotic.

SUMMARY OF THE INVENTION

The present invention provides pharmaceutical compositions useful in treating bacterial infections. Applicant has previously described a series of compounds and pharmaceutical compositions, which have been particularly well-suited for treatment of multi-drug resistant cells, for prevention of the development of multi-drug resistance and for use in multi-drug resistant cancer therapy (U.S. Pat. Nos. 5,330,993, 5,620,971, 5,744,485, 5,543,423 and 5,726,184, the disclosures of which are incorporated herein by reference; and PCT Publications: WO92/19593, WO94/07858, WO92/002278, WO95/26337, WO96/15101, and WO94/07858, the disclosures of which are incorporated herein by reference).

The compositions of the present invention comprise:
(i) an antibiotic;
(ii) a pharmaceutically acceptable carrier; and
(iii) a compound of formula (A-I):

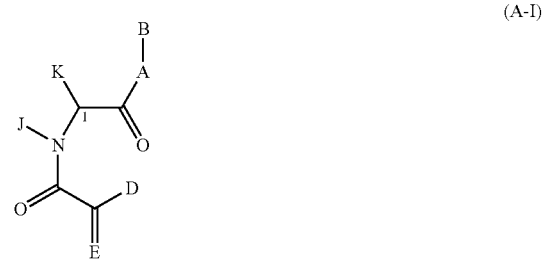

(A-I)

or a pharmaceutically acceptable derivative thereof,
wherein:
A in O, NH, or N—(C1-C4 alkyl);
wherein B is hydrogen, CHL-Ar, (C1-C6)-straight or branched alkyl, (C2-C6)-straight or branched alkenyl, (C5-C7)-cycloalkyl, (C5-C7)-cycloalkenyl or Ar substituted (C1-C6)-alkyl or (C2-C6)-alkenyl, or

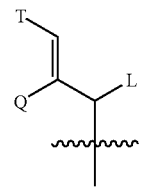

wherein L and Q are independently hydrogen, (C1-C6)-straight or branched alkyl or (C2-C6)-straight or branched alkenyl; and
T is Ar or substituted cyclohexyl with substituents at positions 3 and 4 which are independently selected from the group consisting of hydrogen, hydroxyl, O—(C1-C4)-alkyl or O—(C2-C4)-alkenyl and carbonyl;
wherein Ar is selected from the group consisting of 1-naphthyl, 2-naphthyl, 2-furyl, 3-furyl, 2-thienyl, 2-pyridyl, 3-pyridyl, 4-pyridyl and phenyl having one to three substituents which are independently selected from the group consisting of hydrogen, halo, hydroxyl, nitro, $CF_3$, (C1-C6)-straight or branched alkyl or (C2-C6)-straight or branched alkenyl, O—(C1-C4)-straight or branched alkyl or O—((C2-C4)-straight or branched alkenyl), O-benzyl, O-phenyl, amino and phenyl;
D is U;
E is either oxygen or CH—U, provided that if D is hydrogen, then E is CH—U or if E is oxygen then D is not hydrogen;
wherein each U is independently selected from hydrogen, O—(C1-C4)-straight or branched alkyl or 0-((C2-C4)-straight or branched alkenyl), (C1-C6)-straight or branched alkyl or (C2-C6)-straight or branched alkenyl, (C5-C7)-cycloalkyl or (C5-C7)-cycloalkenyl substituted with (C1-C4)-straight or branched alkyl or (C2-C4)-straight or branched alkenyl, 2-indolyl, 3-indolyl, [(C1-C4)-alkyl or (C2-C4)-alkenyl]-Ar or Ar;

J is hydrogen or C1 or C2 alkyl;

K is (C1-C4)-straight or branched alkyl, benzyl or cyclohexylmethyl; or J and K are taken together to form a 5-7 membered heterocyclic ring which may contain an O, S, SO or $SO_2$ substituent therein; and the stereochemistry at carbon position 1 is R or S.

The compositions of the present invention also comprise:
(i) an antibiotic;
(ii) a pharmaceutically acceptable carrier; and
(iii) a compound having the formula (B-I):

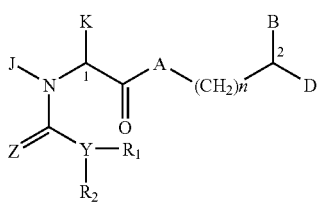

Formula (B-I)

or a pharmaceutically acceptable derivative thereof, wherein:

A is $CH_2$, oxygen, or $NR_1$;

wherein $R_1$, B and D are independently:
hydrogen, Ar, (C1-C6) straight or branched alkyl, (C2-C6) straight or branched alkenyl or alkynyl, (C5-C7) cycloalkyl substituted (C1-C6) straight or branched alkyl, (C5-C7) cycloalkyl substituted (C3-C6) straight or branched alkenyl or alkynyl, (C5-C7) cycloalkenyl substituted (C1-C6) straight or branched alkyl, (C5-C7) cycloalkenyl substituted (C3-C6) straight or branched alkenyl or alkynyl, Ar-substituted (C1-C6) straight or branched alkyl, or Ar-substituted (C3-C6) straight or branched alkenyl or alkynyl;

wherein any one of the $CH_2$ groups of said alkyl chain in $R_1$, B and D is optionally replaced by O, S, SO, $SO_2$ or NR;

wherein R is hydrogen, (C1-C4) straight or branched alkyl, (C3-C4) straight or branched alkenyl or alkynyl, or (C1-C4) bridging-alkyl wherein a bridge is formed between the nitrogen and a carbon atom of said alkyl chain to form a ring, and wherein said ring is optionally fused to Ar;

J is selected from hydrogen, (C1-C6)-straight or branched alkyl, (C3-C6)-straight or branched alkenyl, or —$CH_2Ar$;

K is selected from (C1-C4)-straight or branched alkyl, —$CH_2Ar$, or cyclohexylmethyl; or J and K are taken together with the nitrogen and carbon atoms to which they are respectively bound to form a 5-7 membered heterocyclic ring which may contain a heteroatom selected from O, S, SO and $SO_2$;

Z is O or S;

Y is O or N; wherein
when Y is O, then $R_1$ is a lone pair and $R_2$ is selected from Ar, (C1-C6)-straight or branched alkyl, and (C3-C6)-straight or branched alkenyl or alkynyl; and
when Y is N, then $R_1$ and $R_2$ are independently selected from the group consisting of Ar, (C1-C6)-straight or branched alkyl, and (C3-C6)-straight or branched alkenyl or alkynyl; or $R_1$ and $R_2$ are taken together to form a heterocyclic 5-6 membered ring selected from the group consisting of pyrrolidine, imidazolidine, pyrazolidine, piperidine, and piperazine;

wherein Ar is a carboxylic aromatic group selected from the group consisting of phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thio-phenyl, 1H-indazolyl, benzimidazolyl, benzthiazolyl, purinyl, 4H-quinolizinyl, quinolinyl, 1,2,3,4-tetrahydro-quinolinyl, isoquinolinyl, 1,2,3,4-tetrahydro-isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, or phenoxazinyl;

wherein Ar is optionally substituted with one to three substituents which are independently selected from hydrogen, halogen, hydroxyl, nitro, —$SO_3H$, trifluoromethyl, trifluoromethoxy, (C1-C6)-straight or branched alkyl, (C2-C6)-straight or branched alkenyl, 0-[(C1-C6)-straight or branched alkyl], O[(C3-C4)-straight or branched alkenyl], O-benzyl, O-phenyl, 1,2-methylenedioxy, —$NR_3R_4$, carboxyl, N—(C1-C5-straight or branched alkyl or C3-C5-straight or branched alkenyl) carboxamides, N,N-di-(C1-C5-straight or branched alkyl or C3-C5-straight or branched alkenyl) carboxamides, morpholinyl, piperidinyl, O—Z, $CH_2$—$(CH_2)_q$—Z, O—$(CH_2)_q$—Z, $(CH_2)_q$—Z—O—Z, or CH=CH—Z;

wherein $R_3$ and $R_4$ are independently selected from (C1-C6)-straight or branched alkyl, (C3-C6) straight or branched alkenyl or alkynyl, hydrogen or benzyl; or wherein $R_3$ and $R_4$ are taken together to form a 5-6 membered heterocyclic ring;

wherein Z is selected from 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl;

wherein q is 0-2; and n is 0 or 1.

The compositions of the present invention also comprise:
(i) an antibiotic;
(ii) a pharmaceutically acceptable carrier; and
(iii) a compound of formula (C-I):

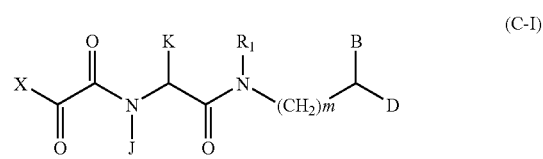

(C-I)

or a pharmaceutically acceptable salt thereof, wherein:

$R_1$, B and D are independently: hydrogen, Ar, (C1-C6) straight or branched alkyl, (C2-C6) straight or branched alkenyl or alkynyl, (C5-C7) cycloalkyl substituted (C1-C6) straight or branched alkyl, (C5-C7) cycloalkyl substituted (C3-C6) straight or branched alkenyl or alkynyl, (C5-C7) cycloalkenyl substituted (C1-C6) straight or branched alkyl, (C5-C7) cycloalkenyl substituted (C3-C6) straight or branched alkenyl of alkynyl, Ar-substituted (C1-C6) straight or branched alkyl, Ar-substituted (C3-C6) straight or branched alkenyl or alkynyl;
provided that $R_1$ is not hydrogen;
wherein any one of the $CH_2$ groups of said alkyl chains in $R_1$, B and D is optionally replaced by O, S, SO, $SO_2$ or NR;
  wherein R is hydrogen, (C1-C6) straight or branched alkyl, (C3-C4) straight or branched alkenyl or alkynyl, or (C1-C4) bridging-alkyl wherein a bridge is formed between the nitrogen and a carbon atom of said alkyl chain to form a ring, and wherein said ring is optionally fused to Ar;
wherein each Ar is independently selected from phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl and phenoxazinyl; and
wherein each Ar is optionally and independently substituted with one to three substituents independently selected from hydrogen, halogen, hydroxyl, nitro, —$SO_3H$, trifluoromethyl, trifluoromethoxy, (C1-C6) straight or branched alkyl, O—((C1-C6) straight or branched alkyl), O-benzyl, O-phenyl, 1,2-methylenedioxy, —$NR_5R_6$, carboxyl, N—(C1-C6 straight or branched alkyl or C3-C5 straight or branched alkenyl) carboxamides, N,N-di-((C1-C6) straight or branched alkyl or (C3-C5) straight or branched alkenyl), carboxamides, morpholinyl, piperidinyl, O-M, $CH_2$—$(CH_2)_q$-M, O—$(CH_2)_q$-M, $(CH_2)_q$—O-M, and CH=CH-M;
  wherein $R_5$ and $R_6$ are independently selected from the group consisting of hydrogen, (C1-C6) straight or branched alkyl, (C2-C6) straight or branched alkenyl or alkynyl, benzyl or $R_5$ and $R_6$ are taken together to form a 5-7 membered heterocyclic ring;
  M is selected from the group consisting of 4-methoxyphenyl, 2-pyridyl, 3-pyridyl, 4-pyridyl, pyrazyl, quinolyl, 3,5-dimethylisoxazoyl, 2-methylthioazoyl, thiazoyl, 2-thienyl, 3-thienyl, 4-thienyl and pyrimidyl; and
  q is 0-2;
J is selected from the group consisting of (C1-C6) straight or branched alkyl, (C3-C6) straight or branched alkenyl or alkynyl, Ar-substituted (C1-C6) straight or branched alkyl, and Ar-substituted (C3-C6) straight or branched alkenyl of alkynyl, and cyclohexylmethyl;
K is selected from the group consisting of (C1-C6) straight or branched alkyl, Ar-substituted (C1-C6) straight or branched alkyl, (C2-C6) straight or branched alkenyl or alkynyl, and Ar-substituted (C3-C6) straight or branched alkenyl or alkynyl; or
  J and K are taken together with the nitrogen and carbon atoms to which they are respectfully bound to form a 5-7 membered heterocyclic ring which may contain a heteroatom selected from O, S, SO and $SO_2$;
X is selected from the group consisting of Ar, —$OR_2$, and —$N(R_3)R_4$;
wherein $R_2$ has the same definition as $R_1$;
$R_3$ and $R_4$ independently have the same definitions as B and D; or $R_3$ and $R_4$ are taken together to form a 5-7 membered heterocyclic aliphatic or aromatic ring; and
m is 0 or 1.

The compositions of the present invention also comprise:
(i) an antibiotic;
(ii) a pharmaceutically acceptable carrier; and
(iii) compound having the formula (D-I):

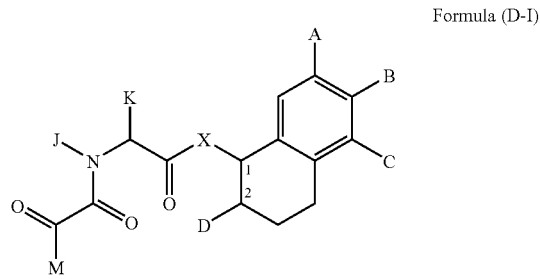

Formula (D-I)

or a pharmaceutically acceptable derivative thereof, wherein A, B, and C are independently:
hydrogen, (C1-C6)-straight or branched alkyl, 0-(C1-C6)-straight or branched alkyl, $(CH_2)$—Ar, $Y(CH_2)$—Ar or halogen, wherein:
  n is 0-4;
  Y is O, S, or $NR_1$;
  $R_1$ is (C1-C6)-straight or branched alkyl or hydrogen;
wherein each Ar is independently selected from phenyl, 1-naphthyl, 2-naphthyl, indenyl, azulenyl, fluorenyl, anthracenyl,
2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl,
2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydro-isoquinolinyl, isoquinolinyl, 1,2,3,4-tetrahydro-isoquinolinyl, cinnolinyl, phthalazinyl, quinazolinyl, quinoxalinyl, 1,8-naphthyridinyl, peridinyl, carbazolyl, acridinyl, phenazinyl, phenothiazinyl or phenoxazinyl;
  wherein each Ar optionally contains one to three substituents independently selected from hydrogen, hydroxyl, halogen, nitro, $SO_3H$, trifluoromethyl, trifluoromethoxy, (C1-C6)-straight or branched alkyl, 0-(C1-C6)-straight or branched alkyl, O-benzyl, O-phenyl, 1,2-methylenedioxy, carboxyl, morpholinyl, piperidinyl and $NR_2R_3$ or $NR_2R_3$ carboxamides;
    wherein $R_2$ and $R_3$ are independently selected from hydrogen, (C1-C5)-straight or branched alkyl or benzyl;

wherein D is selected from hydrogen or (CH$_2$)$_m$-E, wherein:
E is Ar or NR$_4$R$_5$;
m=1-3; and
R$_4$ and R$_5$ are independently selected from hydrogen, alkyl (C1-C5 straight or branched) or (CH$_2$)Ar or can be taken together to form a 5 or 6 membered heterocyclic ring;
wherein X is O or NR$_6$, wherein:
R$_6$ is selected from hydrogen, (C1-C6)-straight or branched alkyl or (CH$_2$)$_m$—Ar;
m=1-3;
wherein J and K are independently (C1-C6)-straight or branched alkyl or Ar-substituted with (C1-C6)-straight or branched alkyl or wherein J and K are taken together to form a five or six membered ring or a five or six membered benzo-fused ring;
wherein M is (C1-C6)-straight or branched alkyl or Ar; and
wherein the stereochemistry at carbon 1 and carbon 2 is R or S.

The present invention also provides a method of treating a bacterial infection in a mammal comprising the step of administering to the mammal a composition of the present invention.

The present invention also provides a method of inhibiting bacterial efflux of an antibiotic, comprising the step of contacting the bacteria with a compound of formula (A-I, B-I, C-I or D-I).

DETAILED DESCRIPTION OF THE INVENTION

Figure 1:
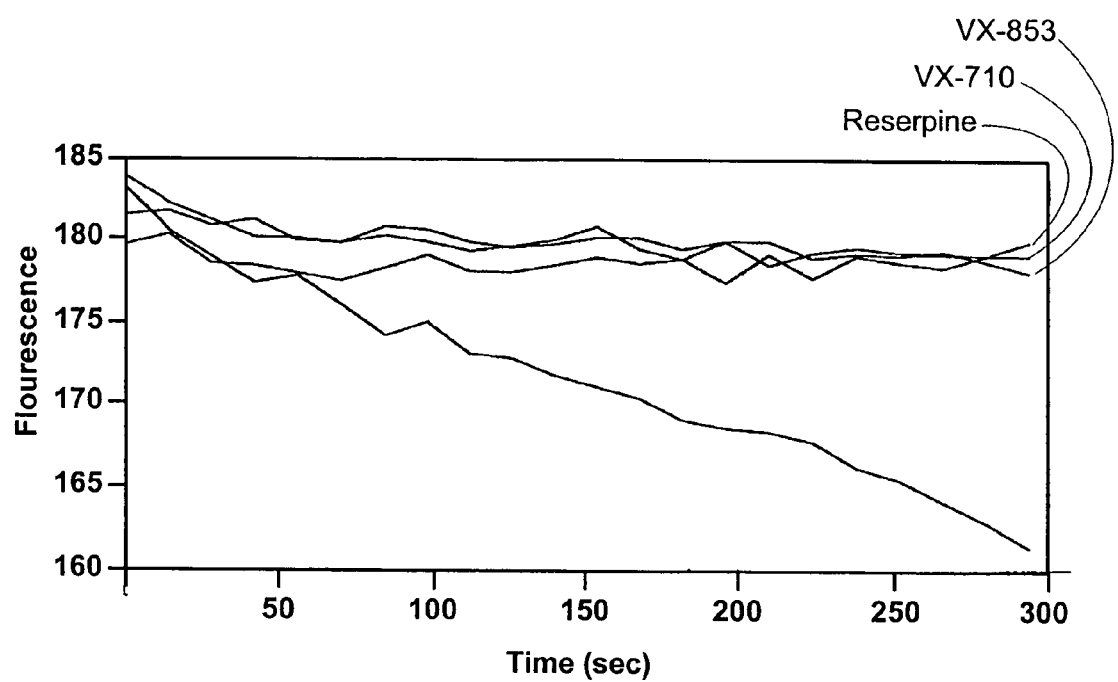
FIG. 1 shows the effect of efflux pump inhibitors (EPIS) on Ethidium Bromide (EtBr) efflux in S. aureus ATCC 29213. S. aureus cells were loaded with EtBr as described in Example 1. EPIs were used at 4XMEC (minimal effective concentration) (25 µg/ml reserpine; 100 µg/ml VX-710 (compound A-106 in Table A-2); 6.25 µg/ml VX-853 (compound C-9 in Table C-I), and no EPI control—as labeled). Fluorescence was continuously monitored over time at room temperature and results are an average of at least 3 replicates.

The present invention provides pharmaceutical compositions useful in treating bacterial infections. The compositions of the present invention comprise:
(i) an antibiotic;
(ii) a pharmaceutically acceptable carrier; and
(iii) a compound of formula (A-I):

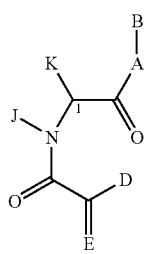

(A-I)

or a pharmaceutically acceptable derivative thereof, wherein:
A in O, NH, or N—(C1-C4 alkyl);
wherein B is hydrogen, CHL-Ar, (C1-C6)-straight or branched alkyl, (C2-C6)-straight or branched alkenyl, (C5-C7)-cycloalkyl, (C5-C7)-cycloalkenyl or Ar substituted (C1-C6)-alkyl or (C2-C6)-alkenyl, or

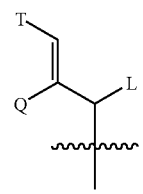

wherein L and Q are independently hydrogen, (C1-C6)-straight or branched alkyl or (C2-C6)-straight or branched alkenyl; and T is Ar or substituted cyclohexyl with substituents at positions 3 and 4 which are independently selected from the group consisting of hydrogen, hydroxyl, O—(C1-C4)-alkyl or O—(C2-C4)-alkenyl and carbonyl;

wherein Ar is selected from the group consisting of 1-naphthyl, 2-naphthyl, 2-furyl, 3-furyl, 2-thienyl, 2-pyridyl, 3-pyridyl, 4-pyridyl and phenyl having one to three substituents which are independently selected from the group consisting of hydrogen, halo, hydroxyl, nitro, CF$_3$, (C1-C6)-straight or branched alkyl or (C2-C6)-straight or branched alkenyl, O—(C1-C4)-straight or branched alkyl or O—((C2-C4)-straight or branched alkenyl), O-benzyl, O-phenyl, amino and phenyl;

D is U;
E is either oxygen or CH—U, provided that if D is hydrogen, then E is CH—U or if E is oxygen then D is not hydrogen;

wherein each U is independently selected from hydrogen, O—(C1-C4)-straight or branched alkyl or O—((C2-C4)-straight or branched alkenyl), (C1-C6)-straight or branched alkyl or (C2-C6)-straight or branched alkenyl, (C5-C7)-cycloalkyl or (C5-C7)-cycloalkenyl substituted with (C1-C4)-straight or branched alkyl or (C2-C4)-straight or branched alkenyl, 2-indolyl, 3-indolyl[(C1-C4)-alkyl or (C2-C4)-alkenyl]-Ar or Ar;

J is hydrogen or C1 or C2 alkyl;

K is (C1-C4)-straight or branched alkyl, benzyl or cyclohexylmethyl; or J and K are taken together to form a 5-7 membered heterocyclic ring which may contain an O, S, SO or SO$_2$ substituent therein; and the stereochemistry at carbon position 1 is R or S.

According to a preferred embodiment, compositions of the present invention comprises a compound selected from any one of Tables A-1a, A-1b, A-1c, or A-II below:

TABLE A-1a (A-1a)

| B | D | n |
|---|---|---|
| Benzyl | Phenyl | 1 |
| Benzyl | Phenyl | 2 |
| Allyl | Phenyl | 2 |
| 1-Naphthyl | Phenyl | 2 |
| 2-Naphthyl | Phenyl | 2 |
| Benzyl | 2-Methylpropyl | 2 |
| Benzyl | 2-Methoxyphenyl | 2 |
| Benzyl | 3-Methoxyphenyl | 2 |
| Benzyl | 4-Methoxyphenyl | 2 |
| Benzyl | 3,5-Dimethoxyphenyl | 2 |
| Benzyl | 2,6-Dimethoxyphenyl | 2 |
| Benzyl | 3,4,5-Trimethoxyphenyl | 2 |
| Benzyl | 4-Fluorophenyl | 2 |
| Benzyl | 3-Nitrophenyl | 2 |
| Benzyl | 4-Nitrophenyl | 2 |
| Benzyl | 2-Pyridyl | 2 |
| Benzyl | 2-pyridyl N-oxide | 2 |
| tert-Butyl | 2-Furyl | 1 |
| Benzyl | 2-Furyl | 2 |
| Benzyl | 3-Indoyl | 2 |
| Benzyl | 2-Thiophenyl | 2 |
| E-3-Phenyl-2-methyl-prop-2-enyl | Phenyl | 2 |
| E-3-(4-Hydroxyphenyl)-2-methyl-prop-2-enyl | Phenyl | 2 |
| E-3-[cis-(4-Hydroxycyclohexyl)]-2-methyl-prop-2-enyl | Phenyl | 2 |
| E-3-[trans-(4-Hydroxycyclohexyl)]-2-methyl-prop-2-enyl | Phenyl | 2 |
| Benzyl | 2-Nitrobenzyl | 2 |
| Hydrogen | Methoxy | 2 |
| tert-Butyl | Methoxy | 1 |
| Allyl | Methoxy | 2 |
| Benzyl | Methoxy | 2 |
| 2-Cyclohexylethyl | Methoxy | 2 |
| 3-Cyclohexylpropyl | Methoxy | 2 |
| 4-Cyclohexylbutyl | Methoxy | 2 |
| 3-Cyclopentylpropyl | Methoxy | 2 |
| E-3-(4-Methoxyphenyl)-2-methyl-prop-2-enyl | Methoxy | 2 |
| E-3-(3,4-Dimethoxyphenyl)-2-methyl-prop-2-enyl | Methoxy | 2 |
| E-3-(4-Hydroxyphenyl)-2-methyl-prop-2-enyl | Methoxy | 2 |
| E-3-[cis-(4-Hydroxycyclohexyl)]-2-methyl-prop-2-enyl | Methoxy | 2 |
| Benzyl | Cyclohexyl | 2 |
| Benzyl | Ethyl | 1 |
| Benzyl | 3-Methoxyphenyl | 1 |
| Benzyl | 2-Pyridyl | 1 |
| Benzyl | 3,4-Difluorophenyl | 2 |
| Benzyl | (E)-2-(4-Methoxyphenyl)-ethenyl | 2 |
| Benzyl | 1-Hydroxy-1-cyclohexyl | 2 |
| Benzyl | 2-Naphthyl | 2 |
| Benzyl | 1-Naphthyl | 2 |
| (S)-alpha-Methylbenzyl | Phenyl | 2 |
| Benzyl | 2-Hydroxy-2-tetrahydropyranyl | 2 |
| (R)-alpha-Methylbenzyl | Phenyl | 2 |
| Benzyl | 3-Trifluoromethylphenyl | 2 |
| Benzyl | 3-Benzyloxyphenyl | 2 |
| Benzyl | (E)-2-tert-Butylethenyl | 2 |
| Benzyl | 2-Trifluoromethylphenyl | 2 |
| 4-Cyclohexylbutyl | Phenyl | 2 |
| 4-Cyclohexylbutyl | 3,4,5-Trimethoxyphenyl | 2 |
| 4-Phenylbenzyl | Phenyl | 2 |
| 4-Phenylbenzyl | 3,4,5-Trimethoxyphenyl | 2 |
| Benzyl | 3-Ethoxyphenyl | 2 |
| 3-Phenoxybenzyl | 3,4,5-Trimethoxyphenyl | 2 |
| 3-Phenoxybenzyl | Phenyl | 2 |
| 4-Phenylbutyl | 3,4,5-Trimethoxyphenyl | 2 |
| 4-Phenylbutyl | Phenyl | 2 |
| Benzyl | 3-(3-Propenyloxy)phenyl | 2 |
| Benzyl | 3-(2-Propoxy)phenyl | 2 |
| Benzyl | 1-Methylpropyl | 2 |
| 2-Phenylethyl | Phenyl | 2 |
| 6-Phenylhexyl | Phenyl | 2 |
| 5-Phenylpentyl | 3,4,5-Trimethoxyphenyl | 2 |
| 6-Phenylhexyl | 3,4,5-Trimethoxyphenyl | 2 |
| 6-Cyclohexylhexyl | 3,4,5-Trimethoxyphenyl | 2 |
| 4-Phenoxybenzyl | 3,4,5-Trimethoxyphenyl | 2 |
| 5-Cyclohexylpentyl | 3,4,5-Trimethoxyphenyl | 2 |
| Benzyl | 3-(1-Butoxy)phenyl | 2 |
| 4-Phenylbutyl | 3-(2-Propoxy)phenyl | 2 |
| 4-(4-Iodophenyl)butyl | 3,4,5-Trimethoxyphenyl | 2 |
| 4-Iodobenzyl | 3,4,5-Trimethoxyphenyl | 2 |
| 2-(2-Naphthyl)ethyl | 3,4,5-Trimethoxyphenyl | 2 |
| 2-(1-Naphthyl)ethyl | 3,4,5-Trimethoxyphenyl | 2 |
| 4-Phenylbutyl | 4-Iodophenyl | 2 |
| 4-Phenylbutyl | 3-Iodophenyl | 2 |
| 3-Phenylpropyl | 3,4,5-Trimethoxyphenyl | 2 |
| 3-(3-Indolyl)propyl | 3,4,5-Trimethoxyphenyl | 2 |
| 4-(4-Methoxyphenyl)butyl | 3,4,5-Trimethoxyphenyl | 2 |
| 4-Phenylbut-2-enyl | 3,4,5-Trimethoxyphenyl | 2 |
| 4-Phenylbut-3-enyl | 3,4,5-Trimethoxyphenyl | 2 |
| 4-(4-Allocaminophenyl)propyl | 3,4,5-Trimethoxyphenyl | 2 |
| 4-Phenylpropyl | 1-Cyclohexenyl | 2 |
| 4-(4-Methoxyphenyl)but-3-enyl | 3,4,5-Trimethoxyphenyl | 2 |
| 4-Phenylpropyl | 1-Fluoro-1-cyclohexyl | 2 |
| 4-Phenylpropyl | 3-Butoxyphenyl | 2 |
| 3-[3-(N-Formylindolyl)]propyl | 3,4,5-Trimethoxyphenyl | 2 |
| 4-(3-indolyl)butyl | 3,4,5-Trimethoxyphenyl | 2 |
| 4-Phenylbutyl | Benzyl | 2 |
| 4-Phenylbutyl | 3-Biphenyl | 2 |
| 4-Phenylbutyl | 4-tert-Butylphenyl | 2 |
| 4-Phenylbutyl | Cyclohexyl | 2 |
| 4-Phenylbutyl | Cyclohexylmethyl | 2 |
| 4-Phenylbutyl | 3,4-Methylenedioxyphenyl | 2 |
| 4-Phenylbutyl | 4-Tetrahydropyranyl | 2 |
| 4-Phenylbutyl | 3-Cyclohexyl-4-methoxy-phenyl | 2 |
| 4-Phenylbutyl | 4-(4-Methoxybenzyloxy-methyl)-2-furyl | 2 |
| 4-Phenylbutyl | tert-Butyl | 2 |
| 4-Phenylbutyl | Ethyl | 2 |
| 3-(N-Benzimidazolyl)propyl | 3,4,5-Trimethoxyphenyl | 2 |
| 3-(N-Purinyl)propyl | 3,4,5-Trimethoxyphenyl | 2 |

TABLE A-1a-continued (A-1a)

| B | D | n |
|---|---|---|
| (S,S)-2-Methyl-3-hydroxy-4-phenylpropyl | 3,4,5-Trimethoxyphenyl | 2 |

TABLE A-1b (A-1b)

| B | U | n |
|---|---|---|
| Benzyl | 3,4-Methylenedioxyphenyl | 1 |
| Benzyl | 3,4-Methylenedioxyphenyl | 2 |
| Benzyl | 4-Methoxyphenyl | 1 |
| Benzyl | 4-Methoxyphenyl | 2 |
| Benzyl | 2,5-Dimethoxyphenyl | 1 |
| Benzyl | 2,4,5-Trimethoxyphenyl | 1 |
| Benzyl | 3,4,5-Trimethoxyphenyl | 1 |
| Benzyl | 4-Dimethylaminophenyl | 2 |
| Benzyl | 4-Nitrophenyl | 2 |
| Benzyl | 1-Furyl | 2 |
| Benzyl | 2-Furyl | 2 |
| Benzyl | 3-Indoyl | 2 |
| Benzyl | 3-Pyridyl | 2 |
| Benzyl | Hydrogen | 2 |
| Benzyl | Phenyl | 2 |

TABLE A-1c (A-1c)

| B | D | J | K |
|---|---|---|---|
| Benzyl | Methoxy | Methyl | Hydrogen |
| Benzyl | Methoxy | Methyl | S-methyl |
| Benzyl | Methoxy | Methyl | S-Isopropyl |
| Ethyl | Methoxy | Benzyl | Hydrogen |
| tert-Butyl | Methoxy | Ethyl | S-Methyl |

TABLE A-1d (A-1d)

| B | U | J | K |
|---|---|---|---|
| Benzyl | 4-methoxyphenyl | Methyl | S-Methyl |
| Benzyl | 4-methoxyphenyl | Methyl | S-Isopropyl |
| Benzyl | 3,4-Methylenedioxyphenyl | Methyl | S-Methyl |
| Benzyl | 3,4-Methylenedioxyphenyl | Hydrogen | S-Methyl |

TABLE A-2

(A-II')

| Cmpd. | n | m | B' | W | Ar' |
|---|---|---|---|---|---|
| A-2 | 1 | 0 | 3-(Pyridin-2-yl) propyl | 3-Phenylpropyl | 3,4,5-Trimethoxyphenyl |
| A-3 | 2 | 0 | 3-Phenylpropyl | 3-Phenylpropyl | 3,4,5-Trimethoxyphenyl |
| A-4 | 2 | 0 | 3-Phenoxyphenyl | 3-Phenylpropyl | 3,4,5-Trimethoxyphenyl |
| A-5 | 2 | 0 | Phenyl | 3-Phenoxyphenyl | 3,4,5-Trimethoxyphenyl |
| A-6 | 2 | 0 | Phenyl | 3-Phenylpropyl | 3,4,5-Trimethoxyphenyl |
| A-7 | 2 | 0 | 2-(Pyridin-3-yl) ethyl | 3-Phenylpropyl | 3,4,5-Trimethoxyphenyl |
| A-8 | 2 | 0 | E-3-[trans-(4-Hydroxycyclohexyl)]-2-methyl-eth-2-enyl | 3-Phenylpropyl | 3,4,5-Trimethoxyphenyl |
| A-9 | 2 | 0 | 3-(Pyridin-3-yl)propyl | 3-Phenylpropyl | 3,4,5-Trimethoxyphenyl |
| A-10 | 2 | 0 | Benzyl | 3-Phenylpropyl | 3,4,5-Trimethoxyphenyl |

TABLE A-2-continued (A-II')

| Cmpd. | n | m | B' | W | Ar' |
|---|---|---|---|---|---|
| A-11 | 2 | 0 | Benzyl | 3-(Indol-3-yl) propyl | 3,4,5-Trimethoxy-phenyl |
| A-12 | 2 | 0 | 2-Phenylethyl | 3-Phenylpropyl | 3,4,5-Trimethoxy-phenyl |
| A-13 | 2 | 0 | 2-(4-Methoxy-phenyl) ethyl | 3-Phenylpropyl | 3,4,5-Trimethoxy-phenyl |
| A-14 | 2 | 0 | 2-(4-Methoxy-phenyl)ethyl | 3-Phenylpropyl | Phenyl |
| A-15 | 2 | 0 | 3-(N-Benzimidazolyl)-propyl | 3-Phenylpropyl | 3,4,5-Trimethoxy-phenyl |
| A-16 | 2 | 1 | Benzyl | 2-Phenylethyl | 3,4,5-Trimethoxy-phenyl |
| A-17 | 2 | 0 | 3-(4-Methoxy-phenyl)propyl | 3-Phenylpropyl | 3,4,5-Trimethoxy-phenyl |
| A-18 | 2 | 0 | 3-(Pyridin-3-yl)-propyl | 3-Phenylpropyl | Phenyl |
| A-19 | 2 | 0 | 3-(Pyridin-2-yl)-propyl | 3-Phenylpropyl | Phenyl |
| A-20 | 2 | 0 | 3-(Pyridin-2-yl)-propyl | 3-Phenylpropyl | 3,4,5-Trimethoxy-phenyl |
| A-21 | 2 | 0 | 3-(Pyridin-2yl)-propyl | 3-Phenylpropyl | tert-Butyl |
| A-22 | 2 | 0 | 3-(Pyridin-3-yl)-propyl-N-oxide | 3-Phenylpropyl | 3,4,5-Tdmethoxy-phenyl |
| A-23 | 2 | 0 | 3-IN-(7-Azaindolyl)-propyl | 3-Phenylpropyl | 3,4,5-Trimethoxy-phenyl |
| A-24 | 2 | 0 | 3-(Pyridin-3-yl)-propyl | 3-(4-Methoxy-phenyl)-propyl | 3,4,5-Trimethoxy-phenyl |
| A-25 | 2 | 0 | 3-(N-Purinyl) propyl | 3-Phenylpropyl | 3,4,5-Trimethoxy-phenyl |
| A-26 | 2 | 0 | 3-(4-Hydroxy-methylphenyl) propyl | 3-Phenylpropyl | 3,4,5-Trimethoxy phenyl |
| A-27 | 2 | 0 | 3-(Pyridin-3-yl)-propyl | 3-Phenylpropyl | 3-Benzyloxy-phenyl |
| A-28 | 2 | 0 | 3-(Pyridin-3-yl)-propyl | 3-Phenylpropyl | 3-Allyloxy-phenyl |
| A-29 | 2 | 0 | 3-(Pyridin-3-yl)-propyl | 3-Phenylpropyl | 3-Isopropoxy-phenyl |
| A-30 | 2 | 0 | 3-(Thiophen-2-yl)-propyl | 3-Phenylpropyl | 3,4,5-Trimethoxy-phenyl |
| A-31 | 2 | 0 | 3-(4-Carboxyphenyl)-propyl | 3-Phenylpropyl | 3,4,5-Trimethoxy-phenyl |
| A-32 | 2 | 0 | 3-Phenylbutyl | 3-Phenylpropyl | 3,4,5-Trimethoxy-phenyl |
| A-33 | 2 | 0 | 2-Hydroxymethyl phenyl | 3-Phenylpropyl | 3,4,6-Trimethoxy-phenyl |
| A-34 | 2 | 0 | 2-Allyloxyphenyl | 3-Phenylpropyl | 3,4,5-Trimethoxy-phenyl |
| A-35 | 2 | 0 | 3-(3-Hydroxymethyl phenyl) propyl | 3-Phenylpropyl | 3,4,5-Trimethoxy-phenyl |
| A-36 | 2 | 0 | 3-(3-Carboxyphenyl) propyl | 3-Phenylpropyl | 3,4,5-Trimethoxy-phenyl |
| A-37 | 2 | 0 | 3-Hydroxymethyl phenyl | 3-Phenylpropyl | 3,4,5-Trimethoxy-phenyl |
| A-38 | 2 | 0 | 2-Hydroxyphenyl | 3-Phenylpropyl | 3,4,5-Trimethoxy-phenyl |
| A-39 | 2 | 0 | Pyridin-3-yl | 3-Phenylpropyl | 3,4,5-Trimethoxy-phenyl |
| A-40 | 2 | 0 | 3-(Thiopen-2-yl)-propyl | 4-Phenylbutyl | 3,4,5-Trimethoxy-phenyl |
| A-41 | 2 | 0 | 5-Phenylpentyl | 3-Phenylpropyl | 3,4,5-Trimethoxy-phenyl |
| A-42 | 2 | 0 | 3-Allyloxypropyl | 3-Phenylpropyl | 3,4,5-Trimethoxy-phenyl |
| A-43 | 2 | 0 | 3-[4-(N,N-Dimethylamine-carbonyl)-phenyl] propyl | 3-Phenylpropyl | 3,4,5-Trimethoxy-phenyl |
| A-44 | 2 | 0 | 3-[4-(Morpholine-4-carbonyl)phenyl]-propyl | 3-Phenylpropyl | 3,4,5-Trimethoxy-phenyl |
| A-45 | 2 | 0 | 4-Alllyoxybutyl | 3-Phenylpropyl | 3,4,5-Trimethoxy-phenyl |
| A-46 | 2 | 0 | 3-Allyloxy-prop-1-ynyl | 3-Phenylpropyl | 3,4,5-Trimethoxy-phenyl |
| A-47 | 2 | 0 | 3-[4-(Piperidine-1-carbonyl)phenyl]-propyl | 3-Phenylpropyl | 3,4,5-Trimethoxy-phenyl |
| A-48 | 2 | 0 | 5-Allyloxynonyl | 3-Phenylpropyl | 3,4,5-Trimethoxy-phenyl |
| A-49 | 2 | 0 | Methyl | 3,5-Bis(benzyloxy) phenyl | 3,4,5-Trimethoxy-phenyl |
| A-50 | 2 | 0 | 2-Allyloxyethyl | 3-Phenylpropyl | 3,4,5-Trimethoxy-phenyl |
| A-51 | 2 | 0 | 3-Allyloxy-(E)-prop-1-ynyl | 3-Phenylpropyl | 3,4,5-Trimethoxy-phenyl |

TABLE A-2-continued (A-II')

| Cmpd. | n | m | B' | W | Ar' |
|---|---|---|---|---|---|
| A-52 | 2 | 0 | 3-[3-(Morpholine-4-carbonyl)phenyl]propyl | 3-Phenylpropyl | 3,4,5-Trimethoxyphenyl |
| A-53 | 2 | 0 | Dec-9-enyl | 3-Phenylpropyl | 3,4,5-Trimethoxyphenyl |
| A-54 | 2 | 0 | 3-[4-(N-Benzyl-aminecarbonyl)-phenyl]propyl | 3-Phenylpropyl | 3,4,5-Trimethoxyphenyl |
| A-55 | 2 | 0 | 3-[4-(Thiomorpholine-4-carbonyl)\phenyl]-propyl | 3-Phenylpropyl | 3,4,5-Trimethoxyphenyl |
| A-56 | 2 | 0 | 3-(Morpholine-4-carbonyl)phenyl- | 3-Phenylpropyl | 3,4,5-Trimethoxyphenyl |
| A-57 | 2 | 0 | 3-[4-(1-Methyl-piperazine-4-carbonyl)phenyl]propyl | 3-Phenylpropyl | 3,4,5-Trimethoxyphenyl |
| A-58 | 2 | 0 | 3-[4-(1-Benzyl-piperazine-4-carbonyl)phenyl]propyl | 3-Phenylpropyl | 3,4,5-Trimethoxyphenyl |
| A-59 | 2 | 0 | 3-[3-(N-Benzyl-aminecarbonyl)phenyl-propyl | 3-Phenylpropyl | 3,4,5-Trimethoxyphenyl |
| A-60 | 2 | 0 | 3-[4-(N-Pyridin-2-yl-aminecarbon-yl)-phenyl]propyl | 3-Phenylpropyl | 3,4,5-Trimethoxyphenyl |
| A-61 | 2 | 0 | Pryidin-3-yl | 3-(Pyridin-3-yl)-propyl | 3,4,5-Trimethoxyphenyl |
| A-62 | 2 | 0 | Prop-2-enyl | 3,4-Bis-(Pyridin-4-ylmethoxy)phenyl | 3,4,5-Trimethoxyphenyl |
| A-63 | 2 | 0 | Pyridin-3-yl | 3-(Pyridin-4-yl-methoxy)-phenyl | 3,4,5-Trimethoxyphenyl |
| A-64 | 2 | 0 | 3-Phenylpropyl | 3-(Pyridin-4-yl-methoxy)-phenyl | 3,4,5-Trimethoxyphenyl |
| A-65 | 2 | 0 | 3-Phenylpropyl | 3,4-Bis-(Pyridin-4-ylmethoxy)phenyl | 3,4,5-Trimethoxyphenyl |
| A-66 | 2 | 0 | Methyl | 3,4-Bis-(Pyridin-4-ylmethoxy)phenyl | 3,4,5-Trimethoxyphenyl |
| A-67 | 2 | 0 | 3-Phenylpropyl | 2,3,4-Tris-(Pyridin-4-ylmethoxy)phenyl | 3,4,5-Trimethoxyphenyl |
| A-68 | 2 | 0 | 3-Phenylpropyl | 3-(Morpholine-4-carbonyl)-4-(Pyridin-4-ylmethoxy)phenyl | 3,4,5-Trimethoxyphenyl |
| A-69 | 2 | 0 | Methyl | 3,4,5-Tris-(Pyridin-4-ylmethoxy)phenyl | 3,4,5-Trimethoxyphenyl |
| A-70 | 2 | 0 | 3-Phenylpropyl | 3,4,5-Tris-(Pyridin-4-ylmethoxy)phenyl | 3,4,5-Trimethoxyphenyl |
| A-71 | 2 | 0 | Methyl | 3,5-Bis-(Pyridin-4-ylmethoxy)phenyl | 3,4,5-Trimethoxyphenyl |
| A-72 | 2 | 0 | 3,5-Bis-(Pyridin-4-ylmethoxy)phenyl | Methyl | 3,4,5-Trimethoxyphenyl |
| A-73 | 2 | 0 | Methyl | 3,5-Bis-(Pyridin-4-yl[methoxy)-4-Methylphenyl | 3,4,5-Trimethoxyphenyl |
| A-74 | 2 | 0 | Ethyl | 3,4,5-Tris-(Pyridin-4-ylmethoxy)phenyl | 3,4,5-Trimethoxyphenyl |
| A-75 | 2 | 0 | 3,4,5-Tris-(Pyridin-4-yl-methoxy)phenyl | Ethyl | 3,4,5-Trimethoxyphenyl |
| A-76 | 2 | 0 | Prop-2-enyl | 3,4,5-Tris-(Pyridin-4-ylmethoxy)phenyl | 3,4,5-Trimethoxyphenyl |
| A-77 | 2 | 0 | Methyl | 3,4,6-Tris-(Pyridin-4-ylmethoxy)phenyl | 3,4-Dimethoxyphenyl |
| A-78 | 2 | 0 | Ethenyl | 3,4,5-Tris-(Pyridin-4-ylmethoxy)phenyl | 3,4,5-Trimethoxyphenyl |
| A-79 | 2 | 0 | 3,4,5-Tris-(Pyridin-4-ylmethoxy)phenyl | Ethenyl | 3,4,5-Trimethoxyphenyl |
| A-80 | 2 | 0 | Propyl | 3,4,5-Tris-(Pyridin-4-ylmethoxy)phenyl | 3,4,5-Trimethoxyphenyl |
| A-81 | 2 | 0 | 3,4,5-Tris-(Pyridin-4-ylmethoxy)phenyl | Propyl | 3,4,5-Trimethoxyphenyl |
| A-82 | 2 | 0 | Methyl | 3,4,5-Tris-(Thiophen-3-ylmethoxy)phenyl | 3,4,5-Trimethoxyphenyl |
| A-83 | 2 | 0 | 3,4,5-Tris-(Thio-phen-3-ylmethoxy)phenyl | Methyl | 3,4,5-Trimethoxyphenyl |
| A-84 | 2 | 0 | Methyl | 2-Isopropoxy-3,4-Bis-(Pyridin-4-ylmethoxy)-phenyl | 3,4,5-Trimethoxyphenyl |
| A-85 | 2 | 0 | 2-Isopropoxy-3,4-Bis-(Pyridin-4-yl-methoxy)phenyl | Methyl | 3,4,5-Trimethoxyphenyl |

TABLE A-2-continued (A-II')

| Cmpd. | n | m | B' | W | Ar' |
|---|---|---|---|---|---|
| A-86 | 1 | 0 | Methyl | 3,4,5-Tris-(Pyridin-4-ylmethoxy)phenyl | 3,4,5-Trimethoxyphenyl |
| A-87 | 1 | 0 | 3,4,5-Tris-(Pyridin-4-ylmethoxy)phenyl | Methyl | 3,4,5-Trimethoxyphenyl |
| A-88 | 2 | 0 | Methyl | 3,4,5-Tris-(Pyrimidin-4-ylmethoxy)phenyl | 3,4,5-Trimethoxyphenyl |
| A-89 | 2 | 0 | Benzyloxymethyl | Benzyloxyphenyl | 3,4,5-Trimethoxyphenyl |
| A-90 | 2 | 0 | Methyl | 3,4,5-Tris-(Benzyloxy)-phenyl | 3,4,5-Trimethoxyphenyl |
| A-91 | 2 | 0 | 3-Phenylpropyl | 3-(Pyridin-3-yl-carbonyl)phenyl | 3,4,5-Trimethoxyphenyl |
| A-92 | 2 | 0 | 3-(Pyridin-3-yl-carbonyl)phenyl | 3-Phenylpropyl | 3,4,5-Trimethoxyphenyl |
| A-93 | 2 | 0 | 3-Phenylpropyl | 3-(Pyridin-4-yl-methoxy)phenyl | 3,4-Dimethoxyphenyl |
| A-94 | 2 | 0 | 3-Phenylpropyl | 3-(Pyridin-4-yl-carbonyl)phenyl | 4-Benzyloxy-3,5-Dimethoxyphenyl |
| A-95 | 2 | 0 | 3-Phenylpropyl | 3-(Pyridin-4-yl-carbonyl)phenyl | 4-Allyloxy-3,5-Dimethoxyphenyl |
| A-96 | 2 | 0 | 3-Phenylpropyl | 3-(Pyridin-4-yl-carbonyl)phenyl | 3-Benzyloxy-4-methoxyphenyl |
| A-97 | 2 | 0 | 3-Phenylpropyl | 3-(Pyridin-4-yl-carbonyl)phenyl | 3-Allyloxy-4-methoxyphenyl |
| A-98 | 2 | 0 | 3-Phenylpropyl | 3-(Pyridin-4-yl-carbonyl)phenyl | 3-[3-Phenyl-(E)-prop-2-enyl]-4-methoxyphenyl |
| A-99 | 2 | 0 | 3-Phenylpropyl | 4-(Pyridin-4-yl-carbonyl)phenyl | 4-Benzyloxy-3,5-Dimethoxyphenyl |
| A-100 | 2 | 0 | 3-Phenylpropyl | 4-(Pyridin-4-yl-carbonyl)phenyl | 3-Benzyloxy-4-methoxyphenyl |
| A-101 | 2 | 0 | 3-Phenylpropyl | 3-(Pyridin-4-yl-carbonyl)phenyl | 3,4,5-Trimethoxyphenyl |
| A-102 | 2 | 0 | 3-Phenylpropyl | 3-(Pyridin-4-yl-carbonyl)phenyl | 3,4-Dimethoxyphenyl |
| A-103 | 2 | 0 | 3-Phenylpropyl | Phenyl | 3-Benzyloxy-4-methoxyphenyl |
| A-104 | 2 | 0 | 3-Phenylpropyl | Phenyl | 4-Benzyloxy-3,5-Dimethoxyphenyl |
| A-105 | 1 | 0 | 3-(Pyridin-3-yl)-propyl | 3-Phenylpropyl | tert-Butyl |
| A-106 | 2 | 0 | 3-(Pyridin-3-yl)-propyl | 3-(Pyridin-3-yl)propyl | 3,4,5-Trimethoxyphenyl |
| A-107 | 1 | 0 | Benzyloxymethyl | Benzyloxymethyl | 3,4,5-Trimethoxyphenyl |
| A-108 | 1 | 0 | 3-(Pyridin-3-yl)-propyl | 3-(Pyridin-3-yl)-propyl | 3,4,5-Trimethoxyphenyl |
| A-109 | 2 | 0 | 3-(Pyridin-3-yl)-propyl | 3-(Pyridin-3-yl)-propyl | Isopropyl |
| A-110 | 2 | 0 | 3-(Pyridin-3-yl)- | 3-(Pyridin-3-yl)- | Thiophen-2-yl |
| A-111 | 2 | 0 | 3-(Pyridin-3-yl)-propyl | 3-(Pyridin-3-yl)-propyl | 3,4-Methylene-dioxyphenyl |
| A-112 | 2 | 0 | 3-(Pyridin-3-yl)-prop-2-ynyl | 3-(Pyridin-3-yl)-prop-2-ynyl | 3,4-Methylene-dioxyphenyl |
| A-113 | 2 | 0 | 3-(Pyridin-3-yl)-prop-2-ynyl | 3-(Pyridin-3-yl)-prop-2-ynyl | 3,4,5-Trimethoxyphenyl |
| A-114 | 2 | 0 | 3-(Pyridin-2-yl)-propyl | 3-(Pyridin-2-yl)-propyl | 3,4,5-Trimethoxyphenyl |
| A-115 | 2 | 0 | Isopropyl | 3,4,5-Tris-(Pyridin-4-ylmethoxy)phenyl | 3,4,5-Trimethoxyphenyl |
| A-116 | 2 | 0 | 3,4,5-Tris-(Pyridin-4-ylmethoxy)phenyl | Isopropyl | 3,4,5-Trimethoxyphenyl |
| A-118 | 2 | 0 | 3,4,5-Tris-(Pyridin-4-ylmethoxy)phenyl | Prop-2-enyl | 3,4,5-Trimethoxyphenyl |

According to a more preferred embodiment, compositions of the present invention comprise any one of compounds Table A-2 above.

More preferably, the present invention provides a pharmaceutical composition comprising:

(i) an antibiotic; and (ii) compound A-108 of Table A-2.

More preferably, the present invention provides a pharmaceutical composition comprising:

(i) an antibiotic; and (ii) compound A-106 of Table A-2.

The compositions of the present invention also comprise:
(i) an antibiotic;
(ii) a pharmaceutically acceptable carrier; and
(iii) a compound having the formula (B-I):

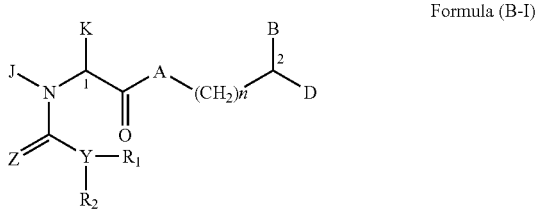

Formula (B-I)

or a pharmaceutically acceptable derivative thereof, wherein:
A is $CH_2$, oxygen, or $NR_1$;
wherein $R_1$, B and D are independently:
hydrogen, Ar, (C1-C6) straight or branched alkyl, (C2-C6) straight or branched alkenyl or alkynyl, (C5-C7) cycloalkyl substituted (C1-C6) straight or branched alkyl, (C5-C7) cycloalkyl substituted (C3-C6) straight or branched alkenyl or alkynyl, (C5-C7) cycloalkenyl substituted (C1-C6) straight or branched alkyl, (C5-C7) cycloalkenyl substituted (C3-C6) straight or branched alkenyl or alkynyl, Ar-substituted (C1-C6) straight or branched alkyl, or Ar-substituted (C3-C6) straight or branched alkenyl or alkynyl;
wherein any one of the $CH_2$ groups of said alkyl chain in $R_1$, B and D is optionally replaced by O, S, SO, $SO_2$ or NR;
wherein R is hydrogen, (C1-C4) straight or branched alkyl, (C3-C4) straight or branched alkenyl or alkynyl, or (C1-C4) bridging-alkyl wherein a bridge is formed between the nitrogen and a carbon atom of said alkyl chain to form a ring, and wherein said ring is optionally fused to Ar;
J is selected from hydrogen, (C1-C6)-straight or branched alkyl, (C3-C6)-straight or branched alkenyl, or —$CH_2$Ar;
K is selected from (C1-C4)-straight or branched alkyl, —$CH_2$Ar, or cyclohexylmethyl; or
J and K are taken together with the nitrogen and carbon atoms to which they are respectively bound to form a 5-7 membered heterocyclic ring which may contain a heteroatom selected from O, S, SO and $SO_2$;
Z is O or S;
Y is O or N; wherein
when Y is O, then $R_1$ is a lone pair and $R_2$ is selected from Ar, (C1-C6)-straight or branched alkyl, and (C3-C6)-straight or branched alkenyl or alkynyl; and
when Y is N, then $R_1$ and $R_2$ are independently selected from the group consisting of Ar, (C1-C6)-straight or branched alkyl, and (C3-C6)-straight or branched alkenyl or alkynyl; or $R_1$ and $R_2$ are taken together to form a heterocyclic 5-6 membered ring selected from the group consisting of pyrrolidine, imidazolidine, pyrazolidine, piperidine, and piperazine;
wherein Ar is a carboxylic aromatic group selected from the group consisting of phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thio-phenyl, 1H-indazolyl, benzimidazolyl, benzthiazolyl, purinyl, 4H-quinolizinyl, quinolinyl, 1,2,3,4-tetrahydro-quinolinyl, isoquinolinyl, 1,2,3,4-tetrahydro-isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, or phenoxazinyl;
wherein Ar is optionally substituted with one to three substituents which are independently selected from hydrogen, halogen, hydroxyl, nitro, —$SO_3H$, trifluoromethyl, trifluoromethoxy, (C1-C6)-straight or branched alkyl, (C2-C6)-straight or branched alkenyl, O-[(C1-C6)-straight or branched alkyl], O[(C3-C4)-straight or branched alkenyl], O-benzyl, O-phenyl, 1,2-methylenedioxy, —$NR_3R_4$, carboxyl, N—(C1-C5-straight or branched alkyl or C3-C5-straight or branched alkenyl) carboxamides, N,N-di-(C1-C5-straight or branched alkyl or C3-C5-straight or branched alkenyl) carboxamides, morpholinyl, piperidinyl, O—Z, $CH_2$—$(CH_2)_q$—Z, O—$(CH_2)_q$—Z, $(CH_2)_q$—Z—O—Z, or CH=CH—Z;
wherein $R_3$ and $R_4$ are independently selected from (C1-C6)-straight or branched alkyl, (C3-C6) straight or branched alkenyl or alkynyl, hydrogen or benzyl; or wherein $R_3$ and $R_4$ are taken together to form a 5-6 membered heterocyclic ring;
wherein Z is selected from 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl;
wherein q is 0-2; and
n is 0 or 1.

According to another embodiment, the composition of the present invention comprises a compound of formula (B-I), wherein at least one of B or D is independently represented by the formula —$(CH_2)_r$—(X)—$(CH_2)_s$—Ar, wherein
r is 1-4;
s is 0-1; and
each X is independently selected from $CH_2$, O, S, SO, $SO_2$, and NR, wherein R is selected from hydrogen, (C1-C4)-straight or branched alkyl, (C3-C4)-straight or branched alkenyl or alkynyl, or (C1-C4) bridging alkyl wherein a bridge is formed between the nitrogen atom and the Ar group.

According to a preferred embodiment, the composition of the present invention comprises a compound having the formula (B-II) or formula (B-III):

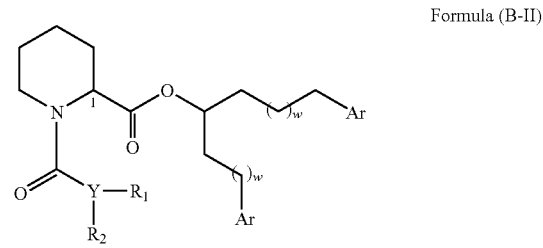

Formula (B-II)

-continued

Formula (B-III)

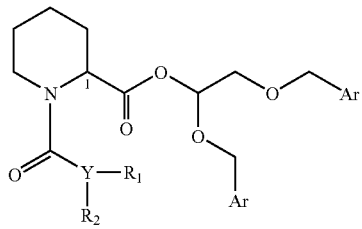

wherein:
w is 1 or 2; and
$Y$, $R_1$, $R_2$, and Ar are as defined above.

According to another embodiment, the compositions of the present invention comprises a compound of formula (B-IV) or formula (B-V):

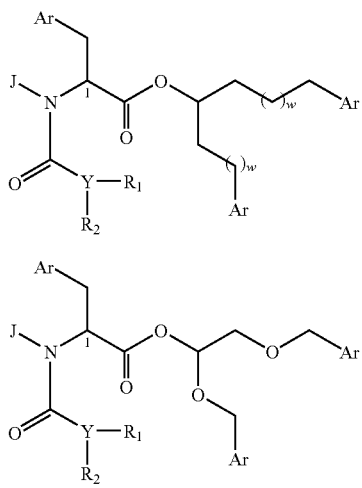

Formula (B-IV)

Formula (B-V)

wherein:
w is 1 or 2; and $Y$, $R_1$, $R_2$, and Ar are as defined above.

According to a preferred embodiment, Ar is selected from substituted or unsubstituted phenyl, 2-pyridyl, 3-pyridyl, 4-pyridyl, indolyl, isoindolyl, quinolinyl, isoquinolinyl, 1,2,3,4-tetrahydroisoquinolinyl, and 1,2,3,4-tetrahydroquinolinyl, and wherein Ar optionally contains one to three substituents which are independently selected from hydrogen, hydroxyl, nitro, trifluoromethyl, (C1-C6)-straight or branched alkyl, O-[(C1-C6)-straight or branched alkyl], halogen, $SO_3H$, or $NR_3R_4$.

More preferably, Ar is substituted or unsubstituted phenyl, 2-pyridyl, 3-pyridyl, 4-pyridyl.

Yet more preferably, Ar is unsubstituted phenyl, 2-pyridyl, 3-pyridyl, or 4-pyridyl.

According to a preferred embodiment, compositions of the present invention comprises a compound selected from:
(S)-1-((3,4,5-Trimethoxyphenyl)-methyl-carbamoyl)-piperidine-2-carboxylic acid 4-pyridin-3-yl-1-(3-pyridin-3-yl-propyl)-butyl ester;
(S)-1-((3-Trifluoromethylphenyl)-methyl-carbamoyl)-piperidine-2-carboxylic acid 4-pyridin-3-yl-1-(3-pyridin-3-yl-propyl)-butyl ester;
(S)-1-((4-Tert-butylphenyl)-methyl-carbamoyl)-piperidine-2-carboxylic acid 4-pyridin-3-yl-1-(3-pyridin-3-yl-propyl)-butyl ester;
(S)-1-((4-Isopropylphenyl)-methyl-carbamoyl)-piperidin-2-carboxylic acid 4-pyridin-3-yl-1-(3-pyridin-3-yl-propyl)-butyl ester;
(S)-1-(Piperidine-1-carbonyl)-piperidine-2-carboxylic acid 4-pyridin-3-yl-1-(3-pyridin-3-yl-propyl)-butyl ester;
(S)-1-((3,4,5-Trimethoxyphenyl)-methyl-carbamoyl)-piperidine-2-carboxylic acid 4-pyridin-1-yl-1-(3-pyridin-1-yl-propyl)-butyl ester;
(S)-Piperidine-1,2-dicarboxylic acid 1-(3,4,5-trimethoxyphenyl)ester-2-(4-pyridin-3-yl-1-(3-pyridin-3-yl-propyl)-butyl)ester;
(S)-1-((3,4,5-Trimethoxyphenyl)-methyl-carbamoyl)-piperidine-2-carboxylic acid 1-(2-phenyl-ethyl)-3-phenyl-propyl ester;
(S)-Piperidine-2-carboxylic acid 2-1-(2-phenyl-ethyl)-3-phenyl-propyl ester;
4-(Methyl-(2-(1-phenethyl-3-phenyl-propoxycarbonyl)-piperidine-1-carbonyl)-amino)-benzenesulfonic acid;
(S)-Piperidine-2-carboxylic acid 1-benzyloxy-methyl-2-benzyloxyethyl ester;
(S)-1-(Methyl-(4-morpholin-1-yl-phenyl)-carbamoyl)-piperidine-2-carboxylic acid 2-benzyloxy-1-(benzyloxy-methyl)-ethyl ester;
(S)-1-(Methyl-(4-piperidin-1-yl-phenyl)-carbamoyl)-piperidine-2-carboxylic acid 2-benzyloxy-1-(benzyloxy-methyl)-ethyl ester;
(S)-Piperidine-1,2-dicarboxylic acid 2-(2-benzyloxy-1-(benzyloxymethyl)-ethyl)ester-1-quinolin-5-yl ester;
(S)-Piperidine-1,2-dicarboxylic acid 2-(2-benzyloxy-1-(benzyloxymethyl)-ethyl)ester-1-pyridin-3-yl ester;
2-(1,3-Dimethyl-3-(3,4,5-trimethoxyphenyl)ureido)-3-phenyl-propanoic acid 4-pyridin-3-yl-1-(3-pyridin-3-yl-propyl)-butyl ester;
2-(1,3-Dimethyl-3-(3,4,5-trimethoxyphenyl)ureido)-3-(phenyl)-propanoic acid 3-pyridin-3-yl-1-(2-pyridin-3-yl-ethyl)-propyl ester;
N-Methyl-2-phenylethylamine-1,2-dicarboxylic acid 1-(3,4,5-trimethoxyphenyl)ester;
2-(4-pyridin-3-yl-1-(3-pyridin-3-yl-propyl)butyl) ester;
N-Methyl-2-phenylethylamine-1,2-dicarboxylic acid 1-(3,4,5-trimethoxyphenyl)ester; or
2-(3-pyridin-3-yl-1-(2-pyridin-3-yl-ethyl)propyl) ester; or pharmaceutically acceptable salts thereof.

The compositions of the present invention also comprise:
(i) an antibiotic;
(ii) a pharmaceutically acceptable carrier; and
(iii) a compound of formula (C-I):

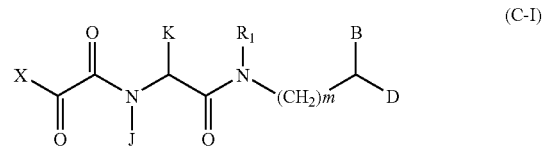

(C-I)

or a pharmaceutically acceptable salt thereof, wherein:
$R_1$, B and D are independently: hydrogen, Ar, (C1-C6) straight or branched alkyl, (C2-C6) straight or branched alkenyl or alkynyl, (C5-C7) cycloalkyl substituted (C1-C6) straight or branched alkyl, (C5-C7) cycloalkyl substituted (C3-C6) straight or branched alkenyl or alkynyl, (C5-C7) cycloalkenyl substituted (C1-C6) straight or branched alkyl, (C5-C7) cycloalkenyl substituted (C3-C6) straight or branched alkenyl of alkynyl, Ar-substituted (C1-C6) straight or branched alkyl, Ar-substituted (C3-C6) straight or branched alkenyl or alkynyl;
provided that $R_1$ is not hydrogen;
wherein any one of the $CH_2$ groups of said alkyl chains in $R_1$, B and D is optionally replaced by O, S, SO, $SO_2$ or NR;
  wherein R is hydrogen, (C1-C6) straight or branched alkyl, (C3-C4) straight or branched alkenyl or alkynyl, or (C1-C4) bridging-alkyl wherein a bridge is formed between the nitrogen and a carbon atom of said alkyl chain to form a ring, and wherein said ring is optionally fused to Ar;
  wherein each Ar is independently selected from phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl and phenoxazinyl; and
  wherein each Ar is optionally and independently substituted with one to three substituents independently selected from hydrogen, halogen, hydroxyl, nitro, —$SO_3H$, trifluoromethyl, trifluoromethoxy, (C1-C6) straight or branched alkyl, O—((C1-C6) straight or branched alkyl), O-benzyl, O-phenyl, 1,2-methylenedioxy, —$NR_5R_6$, carboxyl, N—(C1-C6 straight or branched alkyl or C3-C5 straight or branched alkenyl) carboxamides, N,N-di-((C1-C6) straight or branched alkyl or (C3-C5) straight or branched alkenyl), carboxamides, morpholinyl, piperidinyl, O-M, $CH_2$—$(CH_2)_q$-M, O—$(CH_2)_q$-M, $(CH_2)_q$—O-M, and CH=CH-M;
    wherein $R_5$ and $R_6$ are independently selected from the group consisting of hydrogen, (C1-C6) straight or branched alkyl, (C2-C6) straight or branched alkenyl or alkynyl, benzyl or $R_5$ and $R_6$ are taken together to form a 5-7 membered heterocyclic ring;
    M is selected from the group consisting of 4-methoxyphenyl, 2-pyridyl, 3-pyridyl, 4-pyridyl, pyrazyl, quinolyl, 3,5-dimethylisoxazoyl, 2-methylthioazoyl, thiazoyl, 2-thienyl, 3-thienyl, 4-thienyl and pyrimidyl; and
    q is 0-2;
J is selected from the group consisting of (C1-C6) straight or branched alkyl, (C3-C6) straight or branched alkenyl or alkynyl, Ar-substituted (C1-C6) straight or branched alkyl, and Ar-substituted (C3-C6) straight or branched alkenyl of alkynyl, and cyclohexylmethyl;
K is selected from the group consisting of (C1-C6) straight or branched alkyl, Ar-substituted (C1-C6) straight or branched alkyl, (C2-C6) straight or branched alkenyl or alkynyl, and Ar-substituted (C3-C6) straight or branched alkenyl or alkynyl; or
  J and K are taken together with the nitrogen and carbon atoms to which they are respectfully bound to form a 5-7 membered heterocyclic ring which may contain a heteroatom selected from O, S, SO and $SO_2$;
X is selected from the group consisting of Ar, —$OR_2$, and —$N(R_3)R_4$;
wherein $R_2$ has the same definition as $R_1$;
$R_3$ and $R_4$ independently have the same definitions as B and D; or $R_3$ and $R_4$ are taken together to form a 5-7 membered heterocyclic aliphatic or aromatic ring; and
m is 0 or 1.

According to another embodiment, the composition of the present invention comprises a compound having the formula:

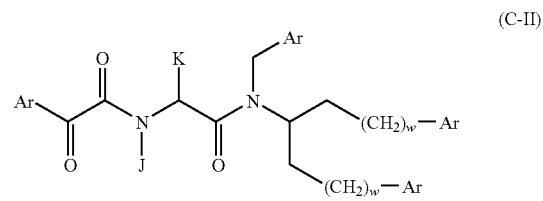

(C-II)

wherein:
  J and K are independently (C1-C6) straight or branched alkyl, or Ar-substituted (C1-C6) straight or branched alkyl; and
  w is 1 or 2.

According to a preferred embodiment, at least one of B or D in compound of formula (C-I) is independently represented by the formula —$(CH_2)_r$-(Z)-$(CH_2)_s$—Ar, wherein:
  r is 1-4;
  s is 0-1; and
  each Z is independently selected from the group consisting of O, S, SO, $SO_2$ and NR; wherein R is selected from the group consisting of hydrogen, (C1-C4) straight or branched alkyl, (C3-C4) straight or branched alkenyl or alkynyl, and (C1-C4) bridging alkyl wherein a bridge if formed between the nitrogen and the Ar group.

According to another embodiment, the compositions of the present invention comprises a compound of formula (C-III):

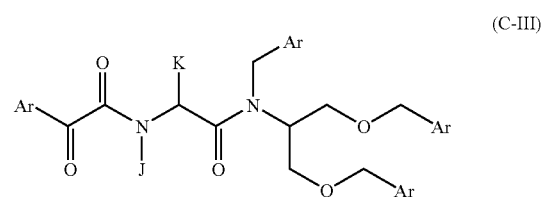

(C-III)

wherein:
  J and K are independently (C1-C6) straight or branched alkyl, or Ar-substituted (C1-C6) straight or branched alkyl; and
  w is 1 or 2.

According to a preferred embodiment, each Ar is independently selected from phenyl, 2-pyridyl, 3-pyridyl, 4-pyridyl, imidazolyl, indolyl, isoindoyl, quinolinyl, isoquinolinyl, 1,2,3,4-tetrahydroisoquinolinyl, or 1,2,3,4-tetrahydroquinolinyl; and
  each Ar optionally and independently contains one to three substituents independently selected from hydroxyl, nitro, trifluoromethyl, (C1-C6) straight or branched alkyl, —O—((C1-C6) straight or branched alkyl), halogen, SO₃H, or —NR₃R₄.

According to a preferred embodiment, compositions of the present invention comprises a compound selected from Table 1 below:

TABLE C-I (C-I')

[Structure: 3,4,5-trimethoxyphenyl-C(=O)-C(=O)-N(CH₃)-CH(K)-C(=O)-N(R₁)-CH(B)(D)]

| Cmpd | B | D | K | R₁ |
|---|---|---|---|---|
| C-6 | 4-Pyr-(CH₂)₂— | 4-Pyr-(CH₂)₂— | PhCH₂— | 4-F—PhCH₂— |
| C-7 | 4-Pyr-(CH₂)₂— | 4-Pyr-(CH₂)₂— | PhCH₂— | PhCH₂— |
| C-8 | 4-Pyr-(CH₂)₂— | 4-Pyr-(CH₂)₂— | PhCH₂— | 4-Cl—PhCH₂— |
| C-9 | 4-Pyr-(CH₂)₂— | 4-Pyr-(CH₂)₂— | 4-Cl—PhCH₂— | PhCH₂— |
| C-10 | H | Ph—(CH₂)₃— | PhCH₂— | 4-PyCH₂— |
| C-12 | 3-Pyr-(CH₂)₃— | 3-Pyr-(CH₂)₃— | PhCH₂— | PhCH₂— |
| C-14 | 4-Pyr-(CH₂)₂— | 4-Pyr-(CH₂)₂— | PhCH₂— | CH₃— |
| C-15 | 3-Pyr-(CH₂)₃— | 3-Pyr-(CH₂)₃— | PhCH₂— | CH₃— |
| C-16 | 4-Pyr-(CH₂)₂— | 4-Pyr-(CH₂)₂— | (CH₃)₂CH—CH₂— | PhCH₂— |
| C-17 | 4-Pyr-(CH₂)₂— | 4-Pyr-(CH₂)₂— | (CH₃)₂CH—CH₂— | 4-F—PhCH₂— |
| C-18 | 4-Pyr-(CH₂)₂— | 4-Pyr-(CH₂)₂— | (CH₃)₂CH—CH₂— | 4-Cl—PhCH₂— |
| C-19 | 4-Pyr-(CH₂)₂— | 4-Pyr-(CH₂)₂— | 4-Cl—PhCH₂— | 4-F—PhCH₂— |
| C-21 | H | 3-lm-(CH₂)₂— | PhCH₂— | PhCH₂— |
| C-23 | Ph—(CH₂)₂— | Ph—(CH₂)₂— | PhCH₂— | 1H-lm-CH₂— |

According to a more preferred embodiment, compositions of the present invention comprise any one of compounds C-6 to C-10, C-12, C-14 to C-19, C-21 or C-23, as defined in Table C-I above.

More preferably, the present invention provides a pharmaceutical composition comprising:
(i) an antibiotic; and
(ii) (S)—N-Benzyl-2-(methyl-(2-oxo-2-(3,4,5-trimethoxyphenyl)acetyl)amino)-3-(4-chloro-phenyl)-N-(3-pyridin-4-yl-1-(2-pyridin-4-yl-ethyl)propyl)propionamide.

More preferably, the present invention provides a pharmaceutical composition comprising:
(i) an antibiotic; and
(ii) compound C-9 of Table C-I.

The compositions of the present invention also comprise:
(i) an antibiotic;
(ii) a pharmaceutically acceptable carrier; and
(iii) compound having the formula (D-I):

Formula (D-I)

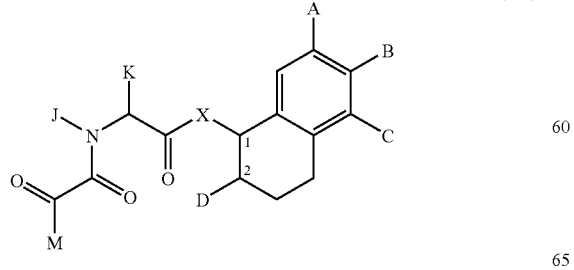

or a pharmaceutically acceptable derivative thereof, wherein

A, B, and C are independently:
hydrogen, (C1-C6)-straight or branched alkyl, 0-(C1-C6)-straight or branched alkyl, (CH₂)ₙ—Ar, Y(CH₂)ₙ—Ar or halogen, wherein:
n is 0-4;
Y is O, S, or NR₁;

R₁ is (C1-C6)-straight or branched alkyl or hydrogen;
wherein each Ar is independently selected from phenyl, 1-naphthyl, 2-naphthyl, indenyl, azulenyl, fluorenyl, anthracenyl,
2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl,
2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, peridinyl, carbazolyl, acridinyl, phenazinyl, phenothiazinyl or phenoxazinyl;
wherein each Ar optionally contains one to three substituents independently selected from hydrogen, hydroxyl, halogen, nitro, SO₃H, trifluoromethyl, trifluoromethoxy, (C1-C6)-straight or branched alkyl, 0-(C1-C6)-straight or branched alkyl, O-benzyl, O-phenyl, 1,2-methylenedioxy, carboxyl, morpholinyl, piperidinyl and NR₂R₃ or NR₂R₃ carboxamides;
wherein R₂ and R₃ are independently selected
from hydrogen, (C1-C5)-straight or branched alkyl or benzyl;
wherein D is selected from hydrogen or (CH₂)ₘ-E, wherein:
E is Ar or NR₄R₅;
m=1-3; and $R_4$ and $R_5$ are independently selected from hydrogen, alkyl (C1-C5 straight or branched) or $(CH_2)Ar$ or can be taken together to form a 5 or 6 membered heterocyclic ring;

wherein X is O or $NR_6$, wherein:
$R_6$ is selected from hydrogen, (C1-C6)-straight or branched alkyl or $(CH_2)_m$—Ar;
m=1-3;

wherein J and K are independently (C1-C6)-straight or branched alkyl or Ar-substituted with (C1-C6)-straight or branched alkyl or wherein J and K are taken together to form a five or six membered ring or a five or six membered benzo-fused ring;

wherein M is (C1-C6)-straight or branched alkyl or Ar; and wherein the stereochemistry at carbon 1 and carbon 2 is R or S.

According to another embodiment, the composition of the present invention comprises a compound having the formula:

Formula (D-II)

wherein M, X, A, B, C, and D are as defined above.

According to a preferred embodiment, the composition of the present invention comprises a compound having the formula:

Formula (D-III)

wherein M, X, A, B, C, and D are as defined above.

According to another embodiment, the compositions of the present invention comprises a compound of formula:

Formula (D-IV)

wherein
M, X, A, B, C, and D are as defined above;
J is methyl or hydrogen; and
K is $(CH_2)_m$—Ar or (C1-C6)-straight or branched alkyl.

According to a preferred embodiment, J is substituted or unsubstituted benzyl.

According to a preferred embodiment, compositions of the present invention comprises a compound selected from Table D-1 below:

TABLE D-I

Formula (D-I)

| Cpd | A | B | C | D | J | K | X |
|-----|---|---|---|---|---|---|---|
| D-6 | OCH$_2$-4Pyr | H | H | H | | | O |
| D-7 | OCH$_2$-4Pyr | H | H | H | | | O |
| D-9 | H | H | OCH$_2$-4Pyr | H | | | O |

TABLE D-I-continued

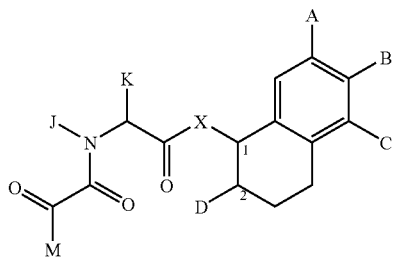

Formula (D-I)

| Cpd | A | B | C | D | J | K | X |
|---|---|---|---|---|---|---|---|
| D-11A | OCH$_2$-4Pyr | H | H | H | | | NH |
| D-11B | OCH$_2$-4Pyr | H | H | H | | | NH |
| D-15 | OCH$_2$-4Pyr | H | H | H | | | N-benzyl |
| D-16 | OCH$_2$-4Pyr | H | H | H | | | N-benzyl |
| D-17 | OCH$_2$-4Pyr | H | H | H | | | O |
| D-18 | OCH$_2$-4Pyr | H | H | H | | | O |
| D-19 | OCH$_2$-4Pyr | H | H | H | H | benzyl | O |
| D-20 | OCH$_2$-4Pyr | H | H | H | CH3 | benzyl | O |
| D-21 | OCH$_2$-4Pyr | H | H | H | CH3 | benzyl | O |
| D-29A | O-propyl | methyl | O-propyl | (CH$_2$)-3-Pyr | | | O |
| D-29B | O-propyl | methyl | O-propyl | (CH$_2$)-3-Pyr | | | O |
| D-30A | O-propyl | methyl | O-propyl | (CH$_2$)-3-Pyr | | | O |
| D-30B | O-propyl | methyl | O-propyl | (CH$_2$)-3-Pyr | | | O |

According to a more preferred embodiment,

A and C are independently selected from —O—CH$_2$-4-pyridine, —O-propyl or hydrogen;

B is selected from —O—CH$_2$-4-pyridine, —O-propyl or hydrogen; and

D is selected from —CH$_2$-3-pyridine or hydrogen.

More preferably, M is 3,4,5-trimethoxyphenyl and X is selected from oxygen, NH$_2$, or N-benzyl.

According to another embodiment, the composition of the present invention comprises an antibiotic selected from ciproflaxacin, levofloxacin, gatifloxacin, moxifloxacin, ofloxacin, norflaxacin, erythromycin, azithromycin, clarithromycin, telithromycin, rifamipin and derivatives thereof, tetracycline, minocycline, chloramphenicol, gentamicin, linezolid, penicillin, amoxicillin, ceftriaxone, or imipenem.

According to another embodiment, the present invention provides a method of treating a bacterial infection in a mammal comprising the step of administering to said mammal a composition of the present invention.

According to a preferred embodiment, the bacterial infection is caused by a gram-positive or a gram-negative bacteria.

According to another preferred embodiment, the the bacterial infection is caused by *Salmonella* spp., *Proteus* spp., *Acinetobacter* spp., *Shigella* spp., *Neisseria* spp., *Enterobacter* spp., *Burkholderia* spp., *Pseudomonas* spp., *Klebsiella* spp., *Haemophilus* spp., *Serratia* spp., *Providencia* spp., *Vibrio* spp., *Francisella* spp., *Yersinia* spp., *Actinobacillus* spp., *Kingella* spp., *Cardiobacterium* spp., *Eikenella corrodens*, *Brucella* spp., *Bartonella* spp., *Vibrio* spp., *Pasteurella* spp., *Edwardsiella* spp., *Aeromonas* spp., *Plesimonas* spp., *Bartonella* spp., *Staphylococcus* spp., *Streptococcus* spp., *Enterococci* spp., *Bacillus* spp., *Corynebacterium* spp, *Actinomyces* spp., *Nocardia* spp., *Rhodococcus* spp., *Aerococcus* spp., *Abiotrophia* spp., *Erysipelotrix* spp., *Listeria* spp., *Archanobacterium* spp., *Mobiluncus* spp., *Gardnerella* spp., *Chlamydia* spp., *Mycoplasma* spp., *Legionella* spp., *Coxiella* spp., *Rickettsia* spp., *Ureaplasma urealyticum*, *Borrelia* spp., *Leptospira* spp., *Treponema* spp., *Bacteroides* spp., *Clostridium* spp., *Helicobacter* spp., *Campylobacter* spp., *Peptostreptococcus* spp., *Fusobacterium* spp, *Propionibacterium* spp., *Prevotella* spp., *Porphyromonas* spp., or *Mycobacteria* spp.

According to another preferred embodiment, the bacterial infection is caused by *Streptococcus* (group A), *Streptococcus* (group C), *Stenotrophomonas maltophilia*, *Archanobacterium haemolyticum*, *Chlamydia pneumoniae*, *Neisseria gonorrhoeae*, *Corynebacterium diphtheriae*, *Corynebacterium ulcerans*, *Mycoplasma pneumoniae*, *Streptococcus pneumoniae*, *Haemophilus influenzae*, *Staphylococcus aureus*, *Moraxella catarrhalis*, *Pseudomonas aeruginosa*, *Bordetella pertussis*, *Bacteroides fragilis*, *Klebsiella pneumoniae*, *Mycobacterium tuberculosis*, *Klebsiella pneumoniae*, *Burkholderia pseudomallei*, *Legionella pneumophila*, *Francisella tularensis*, *Bacteroides fragilis*, *Rhodococcus equi*, *Coxiella burnetti*, *Rickettsia rickettsii*, *E. coli*, *Proteus mirabilis*, *Salmonella typhi*, *Salmonella typhimurium*, *Staphlycoccus saprophyticus*, *Streptococcus* (group B), *Aerococcus urinae*, *Morganella morganii*, *Corynebacterium urealyticum*, *Ureaplasma urealyticum*, *Yersinia enterocolitica*, *Mycobacterium avium*, *Streptococcus viridans* group, *Streptococcus bovis*, *Staphylococcus* coagulase-negative, *Stomatococcus mucilaginosus*, *Actinobacillus actinomycetemcomitans*, *Cardiobacterium hominis*, *Eikenella corrodens*, *Erysipelothrix rhusiopathiae*, *Coxiella burnetii*, *Chlamydia psittaci*, *Corynebacterium diphtheriae*, *Clostridium perfringens*, *Borrelia burgdorferi*, *Neisseria meningitidis*, *Mycoplasma pneumoniae*, *Pseudomonas fluorescens*, *Pseudomonas putida*, *Serratia marcescens*, *Campylobacter jejuni*, *Treponema pallidum*, *Bacillus cerus*, *Listeria monocytogenes*, *Leptospira*, *Rhodococcus equi*, *Vibrio vulnicicus*, *Bacillus anthracis*, *Francisella tularensis*, *Pasterurella multocida*, *Eikenella corrodens*, *Erysipelothrix rhusiopathiae*, *Corynebacterium minutissimum*, *Edwardsiella tarda*, *Bacillus cereus*, *Plesimonas shigelloides*, *Clostridium botulinum*, *Clostridium perfringens*, *Clostridium difficile*, *Streptococcus beta*-hemolytic groups, *Haemophilus ducreyi*, *Chlamydia trachomatis*, *Calymmatobacterium granulomatis*, *Gard-*

*nerella vaginalis, Bartonella henselae, Enterococcus faecalis, Enterococcus faecium, Burkholderia pseudomallei, Treponema carateum*, or *Helicobacter pylori*.

According to another preferred embodiment, the bacterial infection is selected from upper respiratory infections, lower respiratory infections, ear infections, pleuropulmonary and bronchial infections, urinary tract infections, intra-abdominal infections, cardiovascular infections, sepsis, CNS infections, skin and soft tissue infections, GI infections, bone and joint infections, genital infections, eye infections, or granulomatous infections.

According to a more preferred embodiment, the bacterial infection is selected from pharyngitis, sinusitis, otitis externa, otitis media, bronchitis, empyema, pneumonia, cystitis and pyelonephritis, reneal calculi, prostatitis, peritonitis, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, conjunctivitis, keratitis, or endophthalmitis.

The term "bacterial efflux of an antibiotic" as used herein means the extrusion of an antibiotic from within a bacterium. Typically, efflux pumps within bacteria are responsible for such extrusion.

According to another embodiment, the present invention provides a method of inhibiting bacterial efflux of an antibiotic, comprising the step of contracting said bacteria with a compound of formula (A-I):

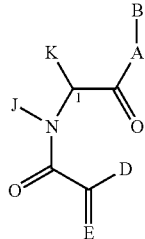

(A-I)

or a pharmaceutically acceptable derivative thereof,
wherein A in O, NH, or N—(C1-C4 alkyl);

wherein B is hydrogen, CHL-Ar, (C1-C6)-straight or branched alkyl, (C2-C6)-straight or branched alkenyl, (C5-C7)-cycloalkyl, (C5-C7)-cycloalkenyl or Ar substituted (C1-C6)-alkyl or (C2-C6)-alkenyl, or

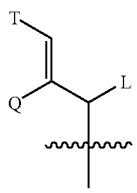

wherein L and Q are independently hydrogen, (C1-C6)-straight or branched alkyl or (C2-C6)-straight or branched alkenyl; and T is Ar or substituted cyclohexyl with substituents at positions 3 and 4 which are independently selected from the group consisting of hydrogen, hydroxyl, O—(C1-C4)-alkyl or O—(C2-C4)-alkenyl and carbonyl;

wherein Ar is selected from the group consisting of 1-naphthyl, 2-naphthyl, 2-furyl, 3-furyl, 2-thienyl, 2-pyridyl, 3-pyridyl, 4-pyridyl and phenyl having one to three substituents which are independently selected from the group consisting of hydrogen, halo, hydroxyl, nitro, $CF_3$, (C1-C6)-straight or branched alkyl or (C2-C6)-straight or branched alkenyl, O—(C1-C4)-straight or branched alkyl or O—((C2-C4)-straight or branched alkenyl), O-benzyl, O-phenyl, amino and phenyl;

D is U;

E is either oxygen or CH—U, provided that if D is hydrogen, then E is CH—U or if E is oxygen then D is not hydrogen;

wherein each U is independently selected from hydrogen, O—(C1-C4)-straight or branched alkyl or O—((C2-C4)-straight or branched alkenyl), (C1-C6)-straight or branched alkyl or (C2-C6)-straight or branched alkenyl, (C5-C7)-cycloalkyl or (C5-C7)-cycloalkenyl substituted with (C1-C4)-straight or branched alkyl or (C2-C4)-straight or branched alkenyl, 2-indolyl, 3-indolyl[(C1-C4)-alkyl or (C2-C4)-alkenyl]-Ar or Ar;

J is hydrogen or C1 or C2 alkyl;

K is (C1-C4)-straight or branched alkyl, benzyl or cyclohexylmethyl; or J and K are taken together to form a 5-7 membered heterocyclic ring which may contain an O, S, SO or $SO_2$ substituent therein; and the stereochemistry at carbon position 1 is R or S.

According to another embodiment, the present invention provides a method of inhibiting bacterial efflux of an antibiotic, comprising the step of contacting said bacteria with a compound of formula (B-I):

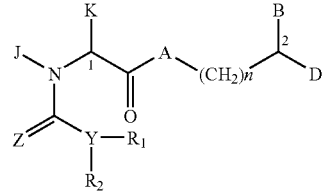

Formula (B-I)

or a pharmaceutically acceptable derivative thereof, wherein:

A is $CH_2$, oxygen, or $NR_1$;

wherein $R_1$, B and D are independently:
hydrogen, Ar, (C1-C6) straight or branched alkyl, (C2-C6) straight or branched alkenyl or alkynyl, (C5-C7) cycloalkyl substituted (C1-C6) straight or branched alkyl, (C5-C7) cycloalkyl substituted (C3-C6) straight or branched alkenyl or alkynyl, (C5-C7) cycloalkenyl substituted (C1-C6) straight or branched alkyl, (C5-C7) cycloalkenyl substituted (C3-C6) straight or branched alkenyl or alkynyl, Ar-substituted (C1-C6) straight or branched alkyl, or Ar-substituted (C3-C6) straight or branched alkenyl or alkynyl;

wherein any one of the $CH_2$ groups of said alkyl chain in $R_1$, B and D is optionally replaced by O, S, SO, $SO_2$ or NR;

wherein R is hydrogen, (C1-C4) straight or branched alkyl, (C3-C4) straight or branched alkenyl or alkynyl, or (C1-C4) bridging-alkyl wherein a bridge is formed between the nitrogen and a carbon atom of said alkyl chain to form a ring, and wherein said ring is optionally fused to Ar;

J is selected from hydrogen, (C1-C6)-straight or branched alkyl, (C3-C6)-straight or branched alkenyl, or —CH$_2$Ar;

K is selected from (C1-C4)-straight or branched alkyl, —CH$_2$Ar, or cyclohexylmethyl; or J and K are taken together with the nitrogen and carbon atoms to which they are respectively bound to form a 5-7 membered heterocyclic ring which may contain a heteroatom selected from O, S, SO and SO$_2$;

Z is O or S;

Y is O or N; wherein when Y is O, then R$_1$ is a lone pair and R$_2$ is selected from Ar, (C1-C6)-straight or branched alkyl, and (C3-C6)-straight or branched alkenyl or alkynyl; and when Y is N, then R$_1$ and R$_2$ are independently selected from the group consisting of Ar, (C1-C6)-straight or branched alkyl, and (C3-C6)-straight or branched alkenyl or alkynyl; or R$_1$ and R$_2$ are taken together to form a heterocyclic 5-6 membered ring selected from the group consisting of pyrrolidine, imidazolidine, pyrazolidine, piperidine, and piperazine;

wherein Ar is a carboxylic aromatic group selected from the group consisting of phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thio-phenyl, 1H-indazolyl, benzimidazolyl, benzthiazolyl, purinyl, 4H-quinolizinyl, quinolinyl, 1,2,3,4-tetrahydro-quinolinyl, isoquinolinyl, 1,2,3,4-tetrahydro-isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, or phenoxazinyl;

wherein Ar is optionally substituted with one to three substituents which are independently selected from hydrogen, halogen, hydroxyl, nitro, —SO$_3$H, trifluoromethyl, trifluoromethoxy, (C1-C6)-straight or branched alkyl, (C2-C6)-straight or branched alkenyl, 0-[(C1-C6)-straight or branched alkyl], O[(C3-C4)-straight or branched alkenyl], O-benzyl, O-phenyl, 1,2-methylenedioxy, —NR$_3$R$_4$, carboxyl, N—(C1-C5-straight or branched alkyl or C3-C5-straight or branched alkenyl) carboxamides, N,N-di-(C1-C5-straight or branched alkyl or C3-C5-straight or branched alkenyl) carboxamides, morpholinyl, piperidinyl, O—Z, CH$_2$—(CH$_2$)$_q$—Z, O—(CH$_2$)$_q$—Z, (CH$_2$)$_q$—Z—O—Z, or CH═CH—Z;

wherein R$_3$ and R$_4$ are independently selected from (C1-C6)-straight or branched alkyl, (C3-C6) straight or branched alkenyl or alkynyl, hydrogen or benzyl; or wherein R$_3$ and R$_4$ are taken together to form a 5-6 membered heterocyclic ring;

wherein Z is selected from 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl;

wherein q is 0-2; and n is 0 or 1.

According to a preferred embodiment, at least one of B or D is independently represented by the formula —(CH$_2$)$_r$—(X)—(CH$_2$)$_s$—Ar, wherein r is 1-4;

s is 0-1; and each X is independently selected from CH$_2$, O, S, SO, SO$_2$, and NR, wherein R is selected from hydrogen, (C1-C4)-straight or branched alkyl, (C3-C4)-straight or branched alkenyl or alkynyl, or (C1-C4) bridging alkyl wherein a bridge is formed between the nitrogen atom and the Ar group.

According to another preferred embodiment, the compound has the (B-II) or formula (B-III):

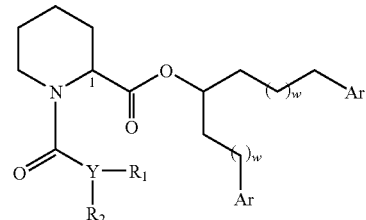

Formula (B-II)

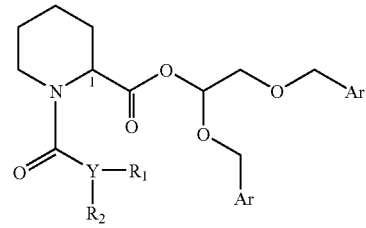

Formula (B-III)

wherein:

w is 1 or 2; and

Y, R$_1$, R$_2$, and Ar are as defined above.

According to another preferred embodiment, the compound has the formula (B-IV) or formula (B-V):

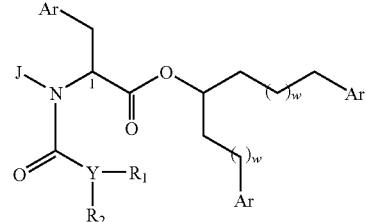

Formula (B-IV)

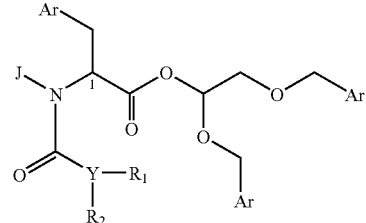

Formula (B-V)

wherein:

w is 1 or 2; and

Y, R$_1$, R$_2$, and Ar are as defined above.

More preferably, Ar is selected from substituted or unsubstituted phenyl, 2-pyridyl, 3-pyridyl, 4-pyridyl, indolyl, isoindolyl, quinolinyl, isoquinolinyl, 1,2,3,4-tetrahydroisoquinolinyl, and 1,2,3,4-tetrahydroquinolinyl, and wherein Ar optionally contains one to three substituents which are independently selected from hydrogen, hydroxyl, nitro, trifluoromethyl, (C1-C6)-straight or branched alkyl, 0-[(C1-C6)-straight or branched alkyl], halogen, $SO_3H$, or $NR_3R_4$ According to a more preferred embodiment:
Ar is substituted or unsubstituted phenyl, 2-pyridyl, 3-pyridyl, 4-pyridyl.

According to a more preferred embodiment, the compound of formula (B-I) is selected from:
(S)-1-((3,4,5-Trimethoxyphenyl)-methyl-carbamoyl)-piperidine-2-carboxylic acid 4-pyridin-3-yl-1-(3-pyridin-3-yl-propyl)-butyl ester;
(S)-1-((3-Trifluoromethylphenyl)-methyl-carbamoyl)-piperidine-2-carboxylic acid 4-pyridin-3-yl-1-(3-pyridin-3-yl-propyl)-butyl ester;
(S)-1-((4-Tert-butylphenyl)-methyl-carbamoyl)-piperidine-2-carboxylic acid 4-pyridin-3-yl-1-(3-pyridin-3-yl-propyl)-butyl ester;
(S)-1-((4-Isopropylphenyl)-methyl-carbamoyl)-piperidin-2-carboxylic acid 4-pyridin-3-yl-1-(3-pyridin-3-yl-propyl)-butyl ester;
(S)-1-(Piperidine-1-carbonyl)-piperidine-2-carboxylic acid 4-pyridin-3-yl-1-(3-pyridin-3-yl-propyl)-butyl ester;
(S)-1-((3,4,5-Trimethoxyphenyl)-methyl-carbamoyl)-piperidine-2-carboxylic acid 4-pyridin-1-yl-1-(3-pyridin-1-yl-propyl)-butyl ester;
(S)-Piperidine-1,2-dicarboxylic acid 1-(3,4,5-trimethoxyphenyl)ester-2-(4-pyridin-3-yl-1-(3-pyridin-3-yl-propyl)-butyl)ester;
(S)-1-((3,4,5-Trimethoxyphenyl)-methyl-carbamoyl)-piperidine-2-carboxylic acid 1-(2-phenyl-ethyl)-3-phenyl-propyl ester;
(S)-Piperidine-2-carboxylic acid 2-1-(2-phenyl-ethyl)-3-phenyl-propyl ester;
4-(Methyl-(2-(1-phenethyl-3-phenyl-propoxycarbonyl)-piperidine-1-carbonyl)-amino)-benzenesulfonic acid;
(S)-Piperidine-2-carboxylic acid 1-benzyloxy-methyl-benzyloxyethyl ester;
(S)-1-(Methyl-(4-morpholin-1-yl-phenyl)-carbamoyl)-piperidine-2-carboxylic acid 2-benzyloxy-1-(benzyloxy-methyl)-ethyl ester;
(S)-1-(Methyl-(4-piperidin-1-yl-phenyl)-carbamoyl)-piperidine-2-carboxylic acid 2-benzyloxy-1-(benzyloxy-methyl)-ethyl ester;
(S)-Piperidine-1,2-dicarboxylic acid 2-(2-benzyloxy-1-(benzyloxymethyl)-ethyl)ester-1-quinolin-5-yl ester;
(S)-Piperidine-1,2-dicarboxylic acid 2-(2-benzyloxy-1-(benzyloxymethyl)-ethyl)ester-1-pyridin-3-yl ester;
2-(1,3-Dimethyl-3-(3,4,5-trimethoxyphenyl)ureido)-3-phenyl-propanoic acid 4-pyridin-3-yl-1-(3-pyridin-3-yl-propyl)-butyl ester;
2-(1,3-Dimethyl-3-(3,4,5-trimethoxyphenyl)ureido)-3-(phenyl)-propanoic acid 3-pyridin-3-yl-1-(2-pyridin-3-yl-ethyl)-propyl ester;
N-Methyl-2-phenylethylamine-1,2-dicarboxylic acid 1-(3,4,5-trimethoxyphenyl)ester;
2-(4-pyridin-3-yl-1-(3-pyridin-3-yl-propyl)butyl) ester;
N-Methyl-2-phenylethylamine-1,2-dicarboxylic acid 1-(3,4,5-trimethoxyphenyl)ester; or
2-(3-pyridin-3-yl-1-(2-pyridin-3-yl-ethyl)propyl) ester; or pharmaceutically acceptable salts thereof.

According to another embodiment, the present invention provides a method of inhibiting bacterial efflux of an antibiotic, comprising the step of contacting said bacteria with a compound of formula (C-I):

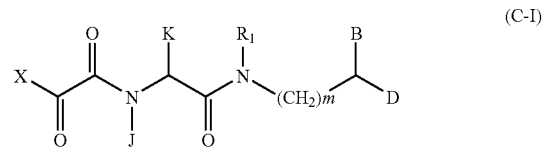

(C-I)

or pharmaceutically acceptable salt thereof, wherein:
$R_1$, B and D are independently: hydrogen, Ar, (C1-C6) straight or branched alkyl, (C2-C6) straight or branched alkenyl or alkynyl, (C5-C7) cycloalkyl substituted (C1-C6) straight or branched alkyl, (C5-C7) cycloalkyl substituted (C3-C6) straight or branched alkenyl or alkynyl, (C5-C7) cycloalkenyl substituted (C1-C6) straight or branched alkyl, (C5-C7) cycloalkenyl substituted (C3-C6) straight or branched alkenyl of alkynyl, Ar-substituted (C1-C6) straight or branched alkyl, Ar-substituted (C3-C6) straight or branched alkenyl or alkynyl;
provided that $R_1$ is not hydrogen;
wherein any one of the $CH_2$ groups of said alkyl chains in $R_1$, B and D is optionally replaced by O, S, SO, $SO_2$ or NR;
wherein R is hydrogen, (C1-C6) straight or branched alkyl, (C3-C4) straight or branched alkenyl or alkynyl, or (C1-C4) bridging-alkyl wherein a bridge is formed between the nitrogen and a carbon atom of said alkyl chain to form a ring, and wherein said ring is optionally fused to Ar;
wherein each Ar is independently selected from phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl and phenoxazinyl; and
wherein each Ar is optionally and independently substituted with one to three substituents independently selected from hydrogen, halogen, hydroxyl, nitro, —$SO_3H$, trifluoromethyl, trifluoromethoxy, (C1-C6) straight or branched alkyl, O—((C1-C6) straight or branched alkyl), O-benzyl, O-phenyl, 1,2-methylenedioxy, —$NR_5R_6$, carboxyl, N—(C1-C6 straight or branched alkyl or C3-C5 straight or branched alkenyl) carboxamides, N,N-di-((C1-C6) straight or branched alkyl or (C3-C5) straight or branched alkenyl), carboxamides, morpholinyl, piperidinyl, O-M, $CH_2$—$(CH_2)_q$-M, 0-$(CH_2)_q$-M, $(CH_2)_q$—O-M, and CH=CH-M;
wherein $R_5$ and $R_6$ are independently selected from the group consisting of hydrogen, (C1-C6) straight or branched alkyl, (C2-C6) straight or branched alkenyl or alkynyl, benzyl or $R_5$ and $R_6$ are taken together to form a 5-7 membered heterocyclic ring;

M is selected from the group consisting of 4-methoxyphenyl, 2-pyridyl, 3-pyridyl, 4-pyridyl, pyrazyl, quinolyl, 3,5-dimethylisoxazoyl, 2-methylthioazoyl, thiazoyl, 2-thienyl, 3-thienyl, 4-thienyl and pyrimidyl; and q is 0-2;

J is selected from the group consisting of (C1-C6) straight or branched alkyl, (C3-C6) straight or branched alkenyl or alkynyl, Ar-substituted (C1-C6) straight or branched alkyl, and Ar-substituted (C3-C6) straight or branched alkenyl of alkynyl, and cyclohexylmethyl;

K is selected from the group consisting of (C1-C6) straight or branched alkyl, Ar-substituted (C1-C6) straight or branched alkyl, (C2-C6) straight or branched alkenyl or alkynyl, and Ar-substituted (C3-C6) straight or branched alkenyl or alkynyl; or J and K are taken together with the nitrogen and carbon atoms to which they are respectfully bound to form a 5-7 membered heterocyclic ring which may contain a heteroatom selected from O, S, SO and $SO_2$;

x is selected from the group consisting of Ar, $-OR_2$, and $-N(R_3)R_4$;

wherein $R_2$ has the same definition as $R_1$;

$R_3$ and $R_4$ independently have the same definitions as B and D; or $R_3$ and $R_4$ are taken together to form a 5-7 membered heterocyclic aliphatic or aromatic ring; and m is 0 or 1.

According to a preferred embodiment, the compound has the formula:

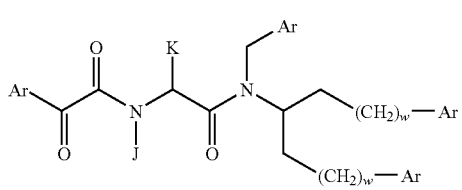

(C-II)

wherein:

J and K are independently (C1-C6) straight or branched alkyl, or Ar-substituted (C1-C6) straight or branched alkyl; and w is 1 or 2.

According to another preferred embodiment, at least one of B or D in formula (C-I) is independently represented by the formula $-(CH_2)_r-(Z)-(CH_2)_s-Ar$, wherein:

r is 1-4;

s is 0-1; and each Z is independently selected from the group consisting of O, S, SO, $SO_2$ and NR; wherein R is selected from the group consisting of hydrogen, (C1-C4) straight or branched alkyl, (C3-C4) straight or branched alkenyl or alkynyl, and (C1-C4) bridging alkyl wherein a bridge if formed between the nitrogen and the Ar group.

According to another preferred embodiment, the compound has the formula:

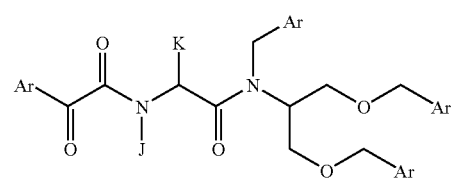

(C-III)

wherein:

J and K are independently (C1-C6) straight or branched alkyl, or Ar-substituted (C1-C6) straight or branched alkyl; and w is 1 or 2.

More preferably, each Ar is independently selected from phenyl, 2-pyridyl, 3-pyridyl, 4-pyridyl, imidazolyl, indolyl, isoindoyl, quinolinyl, isoquinolinyl, 1,2,3,4-tetrahydroisoquinolinyl, or 1,2,3,4-tetrahydroquinolinyl; and each Ar optionally and independently contains one to three substituents independently selected from hydroxyl, nitro, trifluoromethyl, (C1-C6) straight or branched alkyl, O—((C1-C6) straight or branched alkyl), halogen, $SO_3H$, or $-NR_3R_4$.

According to a more preferred embodiment, the compound is selected from any one of compounds C-6 to C-10, C-12, C-14 to C-19, C-21 or C-23, as defined in Table C-I above.

According to a yet more preferred compound, the compound is (S)—N-benzyl-2-(methyl-(2-oxo-2-(3,4,5-trimethoxyphenyl)acetyl)amino)-3-(4-chloro-phenyl)-N-(3-pyridin-4-yl-1-(2-pyridin-4-yl-ethyl)propyl)propionamide.

According to another embodiment, the present invention provides a method of inhibiting bacterial efflux of an antibiotic, comprising the step of contacting said bacteria with a compound of formula (D-I):

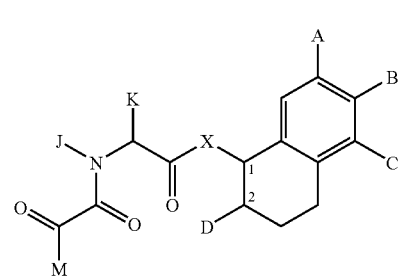

Formula (D-I)

or a pharmaceutically acceptable derivative thereof, wherein A, B, and C are independently:

hydrogen, (C1-C6)-straight or branched alkyl, 0-(C1-C6)-straight or branched alkyl, $(CH_2)_n$—Ar, $Y(CH_2)_n$—Ar or halogen, wherein:

n is 0-4;

Y is O, S, or $NR_1$;

$R_1$ is (C1-C6)-straight or branched alkyl or hydrogen;

wherein each Ar is independently selected from phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, peridinyl, carbazolyl, acridinyl, phenazinyl, phenothiazinyl or phenoxazinyl;

wherein each Ar optionally contains one to three substituents independently selected from hydrogen, hydroxyl, halogen, nitro, $SO_3H$, trifluoromethyl, trifluoromethoxy, (C1-C6)-straight or branched alkyl, 0-(C1-C6)-straight or branched alkyl, O-benzyl, O-phenyl, 1,2-methylenedioxy, carboxyl, morpholinyl, piperidinyl and $NR_2R_3$ or $NR_2R_3$ carboxamides;

wherein $R_2$ and $R_3$ are independently selected from hydrogen, (C1-C5)-straight or branched alkyl or benzyl;

wherein D is selected from hydrogen or $(CH_2)_m$-E, wherein:

E is Ar or $NR_4R_5$;

m=1-3; and $R_4$ and $R_5$ are independently selected from hydrogen, alkyl (C1-C5 straight or branched) or $(CH_2)$Ar or can be taken together to form a 5 or 6 membered heterocyclic ring;

wherein X is O or $NR_6$, wherein:

$R_6$ is selected from hydrogen, (C1-C6)-straight or branched alkyl or $(CH_2)_m$—Ar;

m=1-3;

wherein J and K are independently (C1-C6)-straight or branched alkyl or Ar-substituted with (C1-C6)-straight or branched alkyl or wherein J and K are taken together to form a five or six membered ring or a five or six membered benzo-fused ring;

wherein M is (C1-C6)-straight or branched alkyl or Ar; and wherein the stereochemistry at carbon 1 and carbon 2 is R or S.

According to a preferred embodiment, the compound has the formula:

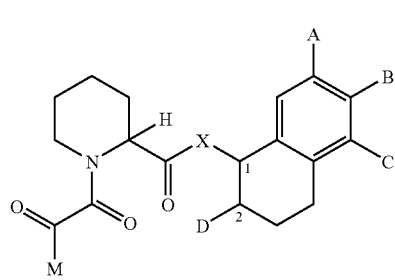

Formula (D-II)

wherein M, X, A, B, C, and D are as defined above.

According to another preferred embodiment, the compound has the formula:

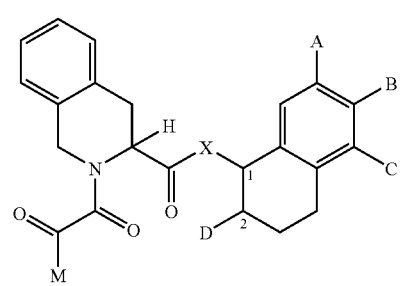

Formula (D-III)

wherein M, X, A, B, C, and D are as defined above;

According to another preferred embodiment, the compound has the formula:

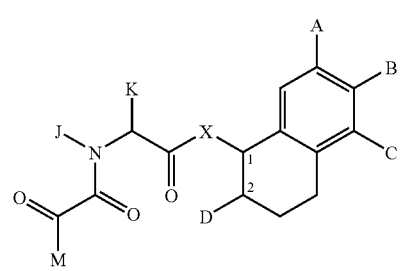

Formula (D-IV)

wherein

M, X, A, B, C, and D are as defined above;

J is methyl or hydrogen; and

K is $(CH_2)_m$—Ar or (C1-C6)-straight or branched alkyl.

More preferably, J is substituted or unsubstituted benzyl.

According to a more preferred embodiment:

M is 3,4,5-trimethoxyphenyl;

X is selected from oxygen, $NH_2$, or N-benzyl;

A and C are independently selected from —O—$CH_2$-4-pyridine, —O-propyl or hydrogen;

B is selected from —O—$CH_2$-4-pyridine, —O-propyl or hydrogen; and

D is selected from —$CH_2$-3-pyridine or hydrogen.

According to a yet more preferred compound, the compound is selected from Table D-1 above.

According to another preferred embodiment, the bacteria is a gram-positive or a gram-negative bacteria.

According to a more preferred embodiment, the gram-positive bacteria is *S. aureus, S. pneumoniae, E. faecalis, E. faecium*, coagulase-negative Staphylococci, *S. pyogenes, M. tuberculosis*, or *Mycobacteria* spp. According to a more preferred embodiment, the gram-negative bacteria is *E. coli, S. typhimurium, P. aeruginosa, K. pneumoniae, H. influenzae*, or *M. catarrhalis*.

According to another preferred embodiment, the the bacterial infection is caused by *Salmonella* spp., *Proteus* spp., *Acinetobacter* spp., *Shigella* spp., *Neisseria* spp., *Enterobacter* spp., *Burkholderia* spp., *Pseudomonas* spp., *Klebsiella* spp., *Haemophilus* spp., *Serratia* spp., *Providencia* spp., *Vibrio* spp., *Francisella* spp., *Yersinia* spp., *Actinobacillus* spp., *Kingella* spp., *Cardiobacterium* spp., *Eikenella corrodens*, *Brucella* spp., *Bartonella* spp., *Vibrio* spp., *Pasteurella* spp., *Edwardsiella* spp., *Aeromonas* spp., *Plesimonas* spp., *Bartonella* spp., *Staphylococcus* spp., *Streptococcus* spp., *Enterococci* spp., *Bacillus* spp., *Corynebacterium* spp, *Actinomyces* spp., *Nocardia* spp., *Rhodococcus* spp., *Aerococcus* spp., *Abiotrophia* spp., *Erysipelotrix* spp., *Listeria* spp., *Archanobacterium* spp., *Mobiluncus* spp., *Gardnerella* spp., *Chlamydia* spp., *Mycoplasma* spp., *Legionella* spp., *Coxiella* spp., *Rickettsia* spp., *Ureaplasma urealyticum*, *Borrelia* spp., *Leptospira* spp., *Treponema* spp., *Bacteroides* spp., *Clostridium* spp., *Helicobacter* spp., *Campylobacter* spp., *Peptostreptococcus* spp., *Fusobacterium* spp, *Propionibacterium* spp., *Prevotella* spp., *Porphyromonas* spp., or *Mycobacteria* spp.

According to another preferred embodiment, the bacteria is selected from *Streptococcus* (group A), *Streptococcus* (group C), *Stenotrophomonas maltophilia*, Archanobacterium haemolyticum, *Chlamydia pneumoniae, Neisseria gonorrhoeae, Corynebacterium diphtheriae, Corynebacterium ulcerans, Mycoplasma pneumoniae, Streptococcus pneumoniae, Haemophilus influenzae, Staphylococcus aureus, Moraxella catarrhalis, Pseudomonas aeruginosa, Bordetella pertussis, Bacteroides fragilis, Klebsiella pneumoniae, Mycobacterium tuberculosis, Klebsiella pneumoniae, Burkholderia pseudomallei, Legionella pneumophila, Francisella tularensis, Bacteroides fragilis, Rhodococcus equi, Coxiella burnetti, Rickettsia rickettsii, E. coli, Proteus mirabilis, Salmonella typhi, Salmonella typhimurium, Staphlycoccus saprophyticus, Streptococcus* (group B), *Aerococcus urinae, Morganella morganii, Corynebacterium urealyticum, Ureaplasma urealyticum, Yersinia enterocolitica, Mycobacterium avium, Streptococcus viridans* group, *Streptococcus bovis, Staphylococcus* coagulase-negative, *Stomatococcus mucilaginosus, Actinobacillus actinomycetemcomitans, Cardiobacterium hominis, Eikenella corrodens, Erysipelothrix rhusiopathiae, Coxiella burnetii, Chlamydia psittaci, Corynebacterium diphtheriae, Clostridium perfringens, Borrelia burgdorferi, Neisseria meningitidis, Mycoplasma pneumoniae, Pseudomonas fluorescens, Pseudomonas putida, Serratia marcescens, Campylobacter jejuni, Treponema pallidum, Bacillus cerus, Listeria monocytogenes, Leptospira, Rhodococcus equi, Vibrio vulnicicus, Bacillus anthracis, Francisella tularensis, Pasterurella multocida, Eikenella corrodens, Erysipelothrix rhusiopathiae, Corynebacterium minutissimum, Edwardsiella tarda, Bacillus cereus, Plesimonas shigelloides, Clostridium botulinum, Clostridium perfringrens, Clostridium difficile, Streptococcus* beta-hemolytic groups, *Haemophilus ducreyi, Chlamydia trachomatis, Calymmatobacterium granulomatis, Gardnerella vaginalis, Bartonella henselae, Enterococcus faecalis, Enterococcus faecium, Burkholderia pseudomallei, Treponema carateum*, or *Helicobacter pylori*.

According to another preferred embodiment, the method of the present invention inhibits the bacterial efflux of an antibiotic selected from ciproflaxacin, levofloxacin, gatifloxacin, moxifloxacin, ofloxacin, norflaxacin, erythromycin, azithromycin, clarithromycin, telitrhomycin, rifamipin and derivatives thereof, tetracycline, minocycline, chloramphenicol, gentamicin, linezolid, penicillin, amoxicillin, ceftriaxone, or imipenem.

If pharmaceutically acceptable salts of the compounds are used, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The third component of the pharmaceutically acceptable compositions of this invention is a pharmaceutically acceptable carrier. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of both, the compound and the antibiotic that may be combined with the carrier materials to produce a single dosage form will vary depending upon the host treated, the particular mode of administration. Therefore, the amount of antibiotic in such compositions will be less than that required in a monotherapy utilizing only that factor. Preferably, the compositions should be formulated so that a dosage of between 0.01-100 mg/kg body weight/day of the compound can be administered and a dosage of between 0.01-100 mg/kg body weight/day of the antibiotic can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and antibiotic present in the composition.

In order that the invention described herein may be more fully understood, the following examples are set forth. It should be understood that these examples are for illustrative purposes only and are not to be construed as limiting this invention in any manner.

Example 1

Experimental Protocol

Compounds.

The compounds of the present invention were prepared using the methods as described in U.S. Pat. Nos. 5,330,993, 5,620,971, 5,744,485, 5,543,423 and 5,726,184 and PCT Publications: WO92/19593, WO94/07858, WO92/002278, WO95/26337, WO96/15101 and WO94/07858, the disclosures of which are incorporated herein by reference. More specifically, VX-710 (formula A-106 in Table A-2) was prepared as described in U.S. Pat. No. 5,543,423 and PCT Publication WO96/15101, and VX-853 (formula C-9 in Table C-I) was prepared as described in U.S. Pat. Nos. 5,330,993 and 5,620971 and PCT Publications WO92/19593, WO94/07858 and WO92/00278. A-106 and C-9 were dissolved in 100% dimethyl sulfoxide (DMSO) at a concentration of 100 mg/ml and stored at −20° C. Reserpine was obtained from Sigma Chemical Co. (St. Louis, Mo.) and stocks were stored as described above. All antibiotics were obtained from standard commercial sources and stocks were prepared at 25.6 mg/ml in 100% DMSO and stored at −20° C.

Bacterial Strains.

A variety of strains may be used in these experiments, including, but not limited to, *S. aureus* ATCC 29213, *E. faecalis* ATCC 29212, and *S. pneumoniae*, *S. aureus* strains SA-1199, SA-1199B, SA-8325-4, and SA-K2068. *S. aureus* ATCC 29213, *E. faecalis* ATCC 29212, and *S. pneumoniae* ATCC 10015 were obtained from the American Type Culture Collection (Manassus, Va.). *S. aureus* strains SA-1199 (clinical isolate, susceptible), SA-1199B (SA-1199, NorA overproducing, also has A116E GrlA mutation), SA-8325-4 (NCTC 8325 cured of prophages), SA-K2068 (SA-8325-4, non-NorA multidrug efflux pump overproducing mutation) were obtained from Glenn Kaatz (Kaatz et al., "Identification and characterization of a novel efflux-related multidrug resistance phenotype in *Staphylococcus aureus*", J. Antimicrob. Chemother. 50:833-838 (2002); 1993; Kaatz et al., "Phenothiazines and thioxanthenes inhibit multidrug efflux pump activity in *Staphylococcus aureus*", Antimicrob. Agents Chemother. 47:719-726, Kaatz et al., "Efflux-mediated fluoroquinolone resistance in *Staphylococcus aureus*. Antimicrob. Agents Chemother.", 37:1086-1094, 1993)).

Antibacterial Assays.

Minimal inhibitory concentrations (MICs) were determined in duplicate or greater by microdilution techniques according to the NCCLS guidelines (National Committee for Clinical Laboratory Standards, "Methods for dilution antimicrobial susceptibility tests for bacteria that grow aerobically—Fifth Edition: Approved Standard M7-A5", NCCLS, Villanova, Pa., USA (2000)) in cation-adjusted Mueller Hinton broth (caMHB, Fisher Scientific, Pittsburgh, Pa.). 3% sterile laked horse blood (Quad Five, Ryegate, Mont.) was added to assays for E. faecalis and S. Pneumoniae. A final concentration of 1% DMSO was present in all assays. This concentration had no antibacterial effect on its own. All antibiotics were obtained from standard commercial sources and antibiotic MICs against quality control strains, S. aureus ATCC 29213, E. faecalis ATCC 29212, and S. pneumoniae ATCC 10015, were within NCCLS ranges (National Committee for Clinical Laboratory Standards, supra).

$MIC_{90}$ Studies.

Susceptibility studies with large panels of resistant clinical isolates were performed at Focus Technologies, Herndon, Va. according to NCCLS protocols (National Committee for Clinical Laboratory Standards, supra). A-106 and C-9 were used at 50 µg/ml in combination with norfloxacin and ciprofloxacin in the presence of 1% DMSO.

Determination of Minimal Effective Concentration (MEC) of Efflux Pump Inhibitors (EPIs).

The MIC of an efflux substrate (EtBr or gatifloxacin) was determined in the presence of increasing amounts of EPI (0 to 100 µg/ml EPI in serial two-fold dilutions). The MEC was determined as the minimal concentration of EPI that produced the maximal reduction in substrate MIC. No further decrease in substrate MIC was observed at EPI concentrations greater than the MEC.

Ethidium Bromide Efflux.

Ethidium bromide (EtBr) efflux assays with S. aureus were performed using the method described by Markham et al. (Markham, et al., "Multiple Novel Inhibitors of the NorA Multidrug Transporter of Staphylococcus aureus", Antimicrob. Agents Chemother. 43:2404-2408 (1999)). Mid-logarithmic phase S. aureus ATCC 29213 in caMHB medium was loaded with 10 µg/ml ethidium bromide in the presence of 25 µg/ml reserpine to inhibit efflux during loading. Cells were grown at 37° C. for 20 minutes and then pelleted by centrifugation. The medium was decanted and the cell pellet was resuspended to an $OD_{600}$ of 0.2 in fresh caMHB medium, both with and without EPI, to an optical density at 600 nanometers of 0.2. Ethidium bromide efflux was determined by continuously monitoring fluorescence at an excitation wavelength of 530 nm and an emission wavelength of 600 nm in a black 96-well polystyrene plate with clear, flat bottom (Costar #3904, Cambridge, Mass.) using a SpectraMax Gemini spectrofluorimeter (Molecular Devices, Sunnydale, Calif.). Results are presented as the average of at least 3 individual replicates.

Activity of Compounds of the Present Invention on the MIC of Ethidium Bromide in S. aureus, E. faecalis and S. pneumoniae.

The activity of A-106 and C-9, compounds of the present invention, were individually evaluated at 100 µg/ml against three wild type gram negative organisms (E. coli, P. aeruginosa, and H. influenzae) and two wild type gram positive organisms (S. aureus and B. subtilis) for activity against efflux of EtBr. EtBr is a general substrate for many different efflux pumps in bacteria. Markham et al., "Multiple Novel Inhibitors of the NorA Multidrug Transporter of Staphylococcus aureus", Antimicrob. Agents Chemother. 43:2404-2408 (1999). Since EtBr is a non-specific DNA intercalator, the only known mechanism of resistance to EtBr is via efflux. Markham et al., "Multiple Novel Inhibitors of the NorA Multidrug Transporter of Staphylococcus aureus", Antimicrob. Agents Chemother. 43:2404-2408 (1999). Standard MIC assays for measuring the antibacterial activity of EtBr were performed in the presence and absence of increasing concentrations of EPI (0 to 100 µg/ml). A-106 and C-9 had no intrinsic antibacterial activity at 100 µg/ml against S. aureus, E. faecalis and S. pneumoniae, while reserpine had an MIC of 50 µg/ml against S. pneumoniae (Table 1). The presence of either A-106 or C-9 reduced the MIC of EtBr in S. aureus and B. subtilis, 30-fold and 8-fold, respectively, suggesting that A-106 or C-9 was blocking efflux of EtBr from cells (data not shown). In contrast, A-106 and C-9 were much less active in all wild type gram-negative organisms; however, some efflux inhibitory activity was observed in permeability mutant strains of E. coli, suggesting that permeability is a limitation to the activity of A-106 or C-9 in E. coli.

The minimum effective concentration (MEC) for inhibition of EtBr efflux was determined in S. aureus, E. faecalis and S. pneumoniae for A-106 and C-9; reserpine was used as a comparator (Table 1). The MIC of EtBr was determined in the presence and absence of increasing amounts of either A-106 or C-9 (0 to 100 µg/ml EPI) in order to determine the minimum concentration of EPI that produced the greatest reduction in EtBr MIC. Results showed increasing amounts of A-106 or C-9 concentration produced better inhibition of EtBr efflux, suggesting that perhaps A-106 and C-9 are acting on more pumps involved in EtBr efflux.

This effect was also observed for reserpine in E. faecalis. For further experiments with EtBr and other antibiotics, unless otherwise noted, A-106 was used at 100 µg/ml, its maximum solubility limit. Since reserpine possessed an intrinsic antibacterial activity in S. pneumoniae at higher concentrations, it is possible that the 50-fold reduction in the MIC of EtBr in the presence of the maximal subinhibitory concentration of reserpine (25 µg/ml) is in part due to a combination of the antibacterial activities of reserpine and EtBr.

Effect of A-106 and C-9 on Ethidium Bromide Efflux in S. aureus ATCC29213

EtBr was used as a test drug to demonstrate directly that A-106 and C-9 could suppress efflux. The ability of A-106 and C-9 to directly inhibit the efflux of EtBr in S. aureus was evaluated using a fluorescence assay. Markham et al., "Multiple Novel Inhibitors of the NorA Multidrug Transporter of Staphylococcus aureus", Antimicrob. Agents Chemother. 43:2404-2408 (1999). Since ethidium only fluoresces when it is bound to nucleic acid inside of cells, a decrease in fluorescence over time is due to active efflux. All EPIs were used at 4 times the MEC for EtBr (Table 1), a saturating concentration in S. aureus ATCC 29213, except for A-106 which was used at 100 µg/ml. Results presented in FIG. 1 are the average of at least triplicate samples. As shown in FIG. 1, only the control cells without A-106 or C-9 inhibitor rapidly extruded EtBr resulting in a substantial decrease in fluorescence over the time of the assay. In the presence of A-106 or C-9, a much more gradual loss of fluorescence was observed, reflecting blockage of EtBr efflux in these samples.

A-106 and C-9 Potentiate the Activity of a Variety of Antibiotics in S. aureus ATCC29213.

One potential clinical advantage conferred by A-106 and C-9 would be to lower the MIC of antibiotics, allowing the use of lower doses to treat infections. A-106 and C-9 were tested at their respective MECs in combination with a variety of different classes of antibiotics against *S. aureus* ATCC 29213 (Table 2). Results showed that, similar to reserpine, A-106 lowered the MICs of levofloxacin, ciprofloxacin, norfloxacin, gentamicin, novobiocin, tetracycline and tetraphenylphophonium bromide by 2- to 4-fold. No effect was observed on the MICs of gatifloxacin, erythromycin, azithromycin, chloramphenicol, ceftriaxone, and linezolid. The results presented in Table 2 reflect the ability of A-106 or C-9 to inhibit the normal level of efflux expression in *S. aureus* ATCC 29213, in the absence of induction by prior antibiotic exposure or any mutation conferring overexpression of efflux pumps.

Hydrophilic fluoroquinolones such as norfloxacin and ciprofloxacin are well-known substrates for the NorA pump and several other less well characterized pumps in *S. aureus* (Kaatz et al., "Efflux-mediated fluoroquinolone resistance in *Staphylococcus aureus*", Antimicrob. Agents Chemother. 37:1086-1094 (1993); Kaatz et al., "Identification and characterization of a novel efflux-related multidrug resistance phenotype in *Staphylococcus aureus*", J. Antimicrob. Chemother. 50:833-838 (2002)). Recent more hydrophobic fluoroquinolones such as gatifloxacin and moxifloxacin are less well recognized by NorA; however, recently one other pump in *S. aureus* has been described which also recognizes hydrophobic fluoroquinolones (Kaatz et al. 2002, supra). To investigate the potential of A-106 and C-9 to block the efflux of several fluoroquinolones in cells with constituitively overexpressed efflux pumps, we used *S. aureus* strains SA-1199B and K2068 (Table 3). All EPIs were used at 4 times the MEC determined for EtBr efflux in *S. aureus* ATCC 29213, except for A-106, which was used at 100 μg/ml, its maximal solubility limit. Results showed that for the NorA overproducing strain (SA-1199B), either A-106 and C-9 were effective in reducing MICs 8- and 32-fold for norfloxacin, 2- and 8-fold for ciprofloxacin, 2- and 4-fold for gatifloxacin, and 1- and 2-fold for levofloxacin. For the non-NorA MDR pump overproducing strain K2068, A-106 and C-9 were also effective in reducing the MICs 2- and 8-fold for norfloxacin, 4- and 8-fold for ciprofloxacin, 2- and 4-fold for gatifloxacin, and 2-fold (by both compounds) for levofloxacin. These results show that A-106 and C-9 are capable of potentiating the antibacterial activities of fluoroquinolones even in the presence of overexpression of efflux, a likely scenario in real clinical *S. aureus* isolates. Substantial reduction of fluoroquinolone MICs occurred in SA-1199B, which in addition to overexpressing NorA also contains a fluoroquinolone-resistant target-based mutation in grlA (A116E). Kaatz et al., "Phenothiazines and thioxanthenes inhibit multidrug efflux pump activity in *Staphylococcus aureus*", Antimicrob. Agents Chemother. 47:719-726 (2003).

Activity EPI Compounds on the Efflux of Gatifloxacin in *S. aureus* MDR Strains.

Since any given compound may be recognized by an unknown number of efflux pumps in a particular organism, we reasoned that the MEC of A-106 and C-9 should vary for different antibiotics. Also, the MEC of A-106 and C-9 should vary with the degree of efflux expression in a given strain. We observed in other experiments (Table 3) that the MIC of gatifloxacin was unaffected by the presence of A-106 or C-9 for wild type strain ATCC 29213, suggesting that the normal level of efflux expression in a wild type strain is not enough to affect the MIC of gatifloxacin. This was confirmed with two other wild type strains, SA-8325-4 and SA-1199 (Table 3). It was also observed in Table 3 that a 4- to 16-fold shift in the MIC of gatifloxacin could only be observed with over-expression of NorA in SA-1199B or a non-NorA pump in K2068, suggesting that gatifloxacin is a poor substrate for these pumps and recognition of gatifloxacin could only be detected with over-expression of efflux proteins.

The MEC of A-106 and C-9 for gatifloxacin was determined in these efflux mutants. Results showed that, as compared to what was seen for EtBr efflux in ATCC 29213 (Table 1, MEC for A-106 $\geqq$100 μg/ml)), the MEC for A-106 was found to be much less (12.5 μg/ml). A similar result was obtained with efflux mutant K2068, where the MEC for A-106 was 6.25 μg/ml and the MEC for C-9 was 3.1 μg/ml. These results show that less A-106 is needed to block gatifloxacin efflux in MDR strains than is required to block EtBr efflux in wild type strains. This may reflect that either gatifloxacin is recognized by fewer pumps than EtBr or it is a poorer efflux substrate in general. This is consistent with the finding that the activity of A-106 was non-saturable for EtBr but is saturable for gatifloxacin.

Results also showed that, as compared to what was seen for EtBr efflux in ATCC 29213, the MEC for C-9 remained similar (3.1 μg/ml, 2-fold difference from value for EtBr in Table 1). A similar result was obtained with efflux mutant K2068, where the MEC for C-9 was 3.1 μg/ml.

Effects of A-106 and C-9 on the Fluoroquinolone Susceptibility of *S. aureus* and *E. faecalis* Clinical Isolate Panels.

To be useful in combination therapy, an EPI needs to substantially reduce the MIC of an antibiotic to within the range of clinical susceptibility. Because many different resistance mechanisms are often present in clinical isolates, including the likelihood of multiple target-based mutations in addition to efflux mutations, the barrier to antibiotic efficacy is much greater. We examined the activity of A-106 and C-9, each at 50 μg/ml, in potentiating the activity of two fluoroquinolones, norfloxacin and ciprofloxacin, against panels of clinical isolates of *S. aureus* and *E. faecalis*, including several high-level fluoroquinolone-resistant mutants (Table 5). This relatively high concentration of EPI approached the solubility limit for both compounds and was chosen to maximize the chance of observing an effect in combination with antibiotics against isolates with multiple resistance mechanisms. Oxacillin and vancomycin MICs were also determined to identify which isolates were methicillin-resistant (*S. aureus*) and vancomycin-resistant (*E. faecalis*). Among the *S. aureus* isolates (Table 5A), >2-fold decreases in the MICs for ciprofloxacin (10/15 isolates) and norfloxacin (13/15 isolates) in combination with A-106 were observed; no significant (>2-fold) decrease in MIC was seen with C-9. Significant increases in ciprofloxacin (isolates # 3 and 5) and norfloxacin MICs (isolates # 3,6,9) in combination with C-9 were observed for several *S. aureus* isolates, while reductions in MICs occurred with A-106 and the same isolates. Less of an effect was observed with both A-106 and C-9 and the *E. faecalis* isolates tested (Table 5B); however, a two-fold trend in the reduction of MICs for ciprofloxacin and norfloxacin in combination with A-106 was observed. A similar trend was less apparent with C-9. While A-106 was generally more active in *S. aureus* than in *E. faecalis*, the activity was still insufficient to restore clinical susceptibility to the highly fluoroquinolone-resistant strains in the panel. A-106 did significantly impact the fluoroquinolone MICs (4- to >8-fold) in the more susceptible *S. aureus* strains in the panel, suggesting a possible use in combination with fluoroquinolones in treating susceptible isolates.

Advantage of Efflux Pump Inhibitors of the Present Invention.

One advantage of this new class of EPIs is that A-106 has already been evaluated for safety in the clinic and in combination with chemotherapeutic agents for cancer therapies. In these studies only mild adverse events were observed for A-106 (Bramwell et al., "Safety and efficacy of the multidrug-resistance inhibitor biricodar (A-106) and concurrent doxorubicin in patients with anthracycline-resistant advanced soft tissue sarcoma", Clin. Cancer. Res. 8:383-393 (2002); Peck et al., "Phase 1 and pharmacokinetic study of the novel MDR1 and MRP1 inhibitor biricodar administered alone and in combination with doxorubicin", J. Clin. Oncol. 19:3130-3141 (2001); Rowinsky et al., "Phase I and pharmacokinetic study of paclitaxel in combination with biricodar, a novel agent that reverses multidrug resistance conferred by overexpression of both MDR1 and MRP", J. Clin. Oncol. 16:2964-2976 (1998); Toppmeyer et al., "Safety and efficacy of the multidrug resistance inhibitor Incel (Biricodar; A-106) in combination with paclitaxel for advanced breast cancer refractory to paclitaxel", Clin. Cancer Res. 8:670-678 (2002)) as compared to other EPIs (Renau et al., "Conformationally-restricted analogues of efflux pump inhibitors that potentiate the activity of levofloxacin in *Pseudomonas aeruginosa*", Bioorg. Med. Chem. Lett. 13:2755-2758 (2003)).

TABLE 1

Effect of efflux pump inhibitors (EPIs) on the antibacterial activity of ethidium bromide in *S. aureus* ATCC 29213, *E. faecalis* ATCC 29212, and *S. pneumoniae* ATCC 10015

| EPI | EPI µg/ml | MEC[a] of EPI µg/ml | MIC of EtBr (µg/ml) without EPI | MIC of EtBr (µg/ml) with EPI[b] | Fold-reduction in EtBr MIC |
|---|---|---|---|---|---|
| A. *S. aureus* | | | | | |
| reserpine | >100 | 6.3 | 6.3 | 1.6 | 4 |
| VX-710 | >100 | ≧100 | 6.3 | 0.2 | 31 |
| VRT-010367 | >50 | 1.6 | 6.2 | 3.1 | 2 |
| VX-853 | >100 | 1.6 | 6.3 | 1.6 | 4 |
| VRT-013661 | >100 | 3.1 | 6.2 | 1.6 | 4 |
| B. *E. faecalis* | | | | | |
| reserpine | >100 | ≧100 | 6.3 | 0.8 | 8 |
| VX-710 | >100 | ≧100 | 6.3 | 0.8 | 8 |
| VX-853 | >100 | 6.3 | 6.3 | 3.1 | 2 |
| C. *S. pneumoniae* | | | | | |
| reserpine | 50 | 25[c] | 2 | 0.04 | 50 |
| VX-710 | >100 | ≧100 | 2 | ≦0.125 | ≧16 |
| VX-853 | >100 | 12.5 | 2 | 1 | 2 |

VRT-10367 is compound A-9 in Table A-2
VRT-013661 is compound C-7 in Table C-I

[a]MEC is the minimum effective EPI concentration, the lowest amount of EPI which produces the maximum effect on the MIC of ethidium bromide.
[b]EPIs were used at the MEC, except for VX-710 which was used at its solubility limit, 100 µg/ml
[c]Maximal subinhibitory concentration of reserpine.

TABLE 2

Potentiation of antibiotic activity by EPIs in *S. aureus* ATCC 29213[b]

| Antibacterial Agent | No EPI | MIC (µg/ml) in the presence of 4X MEC of EPI[a] reserpine | VX-710 | VX-853 |
|---|---|---|---|---|
| EtBr | 6.2 | 1.6 | 0.2 | 1.6 |
| tetracycline | 0.25 | 0.25 | 0.125 | 0.25 |
| novobiocin | 0.125 | 0.063 | 0.063 | 0.063 |
| levofloxacin | 0.25 | 0.125 | 0.125 | 0.125 |
| ciprofloxacin | 0.25 | 0.063 | 0.063 | 0.125 |
| norfloxacin | 1 | 0.5 | 0.25 | 0.5 |
| gentamicin | 0.5 | 0.125 | 0.125 | 0.25 |
| gatifloxacin | 0.125 | 0.125 | 0.125 | 0.125 |
| chloramphenicol | 8 | 8 | 8 | 8 |
| erythromycin | 0.25 | 0.25 | 0.25 | 0.25 |
| ceftriaxone | 4 | 4 | 4 | 4 |
| azithromycin | 1 | 1 | 1 | 1 |
| linezolid | 4 | 4 | 4 | 4 |
| tetraphenyl-phosphonium bromide | 16 | 8 | 4 | 8 |

[a]MEC is the minimal effective concentration determined for EtBr with ATCC29213 in Table 1. Concentrations used (4X MEC): reserpine, 25 µg/ml; VX-710, 100 µg/ml; VX-853, 6.25 µg/ml.
[b]Results were reproduced in a minimum of 2 independent experiments.

TABLE 3

Activity of VX-710 and VX-853 on the MICs of clinically used fluoroquinones in susceptible and resistant *S. aureus* strains[b]

| Antibacterial Agent | EPI[a] | *S. aureus* Strain MIC (µg/ml) ATCC 29213 | SA-1199 | SA-1199B[c] | SA-8325-4 | K2068[d] |
|---|---|---|---|---|---|---|
| EtBr | none | 6.2 | 6.2 | 25 | 3.1 | 12.5 |
| | reserpine | 0.4 | 0.4 | 0.8 | 0.4 | 1.6 |
| | VX-710 | 0.2 | 0.2 | 0.4 | <0.1 | 0.4 |
| | VX-853 | 0.8 | 1.6 | 3.1 | 0.8 | 3.1 |
| norfloxacin | none | 0.5 | 0.5 | 64 | 1 | 8 |
| | reserpine | 0.25 | 0.125 | 4 | 0.25 | 1 |
| | VX-710 | 0.125 | 0.125 | 2 | 0.25 | 1 |

TABLE 3-continued

Activity of VX-710 and VX-853 on the MICs of clinically used fluoroquinones in susceptible and resistant S. aureus strains[b]

| Antibacterial Agent | EPI[a] | ATCC 29213 | SA-1199 | SA-1199B[c] | SA-8325-4 | K2068[d] |
|---|---|---|---|---|---|---|
| | VX-853 | 0.5 | 0.25 | 8 | 0.25 | 4 |
| ciprofloxacin | none | 0.25 | 0.25 | 4 | 0.25 | 4 |
| | reserpine | 0.063 | 0.063 | 0.5 | 0.125 | 0.5 |
| | VX-710 | 0.063 | 0.063 | 0.5 | 0.125 | 0.5 |
| | VX-853 | 0.125 | 0.125 | 2 | 0.125 | 1 |
| levofloxacin | none | 0.25 | 0.125 | 1 | 0.25 | 1 |
| | Reserpine | 0.125 | 0.125 | 0.5 | 0.25 | 0.5 |
| | VX-710 | 0.125 | 0.125 | 0.5 | 0.25 | 0.5 |
| | VX-853 | 0.125 | 0.125 | 1 | 0.25 | 0.5 |
| gatifloxacin | none | 0.063 | 0.063 | 0.5 | 0.125 | 1 |
| | reserpine | 0.063 | 0.063 | 0.125 | 0.125 | 0.25 |
| | VX-710 | 0.063 | 0.063 | 0.125 | 0.125 | 0.25 |
| | VX-853 | 0.063 | 0.063 | 0.25 | 0.125 | 0.5 |
| gentamicin | none | 0.5 | 0.5 | 0.5 | 0.125 | 0.063 |
| | Reserpine | 0.125 | 0.125 | 0.125 | 0.063 | 0.063 |
| | VX-710 | 0.125 | 0.125 | 0.125 | 0.063 | 0.063 |
| | VX-853 | 0.125 | 0.125 | 0.125 | 0.063 | 0.063 |

[a]EPIs were used at 4X the MEC determined for EtBr with ATCC29213 in Table 1, except for VX-710 which was used at 100 µg/ml, its solubility limit.
[b]Results were reproduced in a minimum of 2 independent experiments.
[c]S. aureus mutant, NorA overproducer, GrlAA116E
[d]S. aureus mutant, non-NorA MDR pump overproducer

TABLE 4

Activity of Efflux Pump Inhibitors (EPIs) on the Efflux of Gatifloxacin on S. aureus ATCC 29213, SA-1199B and K2068.

| EPI | MEC* µg/ml | MIC of Gatifloxacin (ug/ml) without EPI | MIC of Gatifloxacin (ug/ml) with EPI | Fold-reduction in MIC |
|---|---|---|---|---|
| A. ATCC 29213** | | | | |
| Reserpine | >100 | 0.125 | 0.125 | 1 |
| VX-710 | >100 | 0.125 | 0.125 | 1 |
| VX-853 | >100 | 0.125 | 0.125 | 1 |
| B. SA-1199B (NorA overproducer) | | | | |
| Reserpine | 25 | 0.5 | 0.25 | 2 |
| VX-710 | 12.5 | 0.5 | 0.25 | 2 |
| VX-853 | 3.1 | 0.5 | 0.25 | 2 |
| C. K2068 (nonNorA pump overproducer) | | | | |
| Reserpine | 3.1 | 1 | 0.25 | 4 |
| VX-710 | 6.25 | 1 | 0.25 | 4 |
| VX-853 | 3.1 | 1 | 0.5 | 2 |

*MEC, the minimum effective EPI concentration is the lowest amount of EPI which produces the maximum effect on the MIC of gatifloxacin.
**Note results were identical for two other wild type S. aureus strains SA-8325-4 and SA-1199.

TABLE 5

Effect of VX-710 and VX-853 on fluoroquinolone S. aureus and E. faecalisc clinical isolates[b]

A.

| S. aureus Isolate | Ciprofloxacin (µg/ml) | | | Norfloxacin (µg/ml) | | | Oxacillin (µg/ml)[a] |
|---|---|---|---|---|---|---|---|
| | No EPI | VX-710 | VX-853 | No EPI | VX-710 | VX-853 | No EPI |
| 1 | 2 | 0.5 | 1 | 16 | 2 | 8 | 16 |
| 2 | 0.5 | 0.12 | 0.5 | 1 | ≦0.25 | 1 | >64 |
| 3 | 0.12 | ≦0.06 | 1 | 1 | ≦0.25 | 4 | 32 |
| 4 | >64 | 64 | 64 | 256 | 128 | 128 | >64 |
| 5 | 0.12 | ≦0.06 | 1 | 1 | ≦0.25 | 2 | 2 |
| 6 | 16 | 8 | 32 | 32 | 8 | 128 | 16 |
| 7 | 0.25 | ≦0.06 | 0.5 | 2 | ≦0.25 | 2 | 2 |
| 8 | 0.5 | 0.25 | 1 | 4 | 1 | 4 | 4 |
| 9 | 0.5 | ≦0.06 | 1 | 1 | ≦0.25 | 4 | 2 |

TABLE 5-continued

Effect of VX-710 and VX-853 on fluoroquinolone
S. aureus and E. faecalisc clinical isolates[b]

| | | | | | | |
|---|---|---|---|---|---|---|
| 10 | 16 | 8 | 16 | 64 | 16 | 64 | >64 |
| 11 | 16 | 8 | 32 | 64 | 32 | 64 | >64 |
| 12 | 0.5 | ≦0.06 | 0.25 | 1 | ≦0.25 | 1 | 2 |
| 13 | >64 | 32 | 64 | 256 | 64 | 128 | >64 |
| 14 | >64 | 32 | 64 | 256 | 64 | 128 | >64 |
| 15 | >64 | 32 | >64 | 256 | 64 | 256 | >64 |

B.

| E. faecalis | Ciprofloxacin (µg/ml) | | | Norfloxacin (µg/ml) | | | Vancomycin (µg/ml)[c] |
|---|---|---|---|---|---|---|---|
| Isolate | No EPI | VX-710 | VX-853 | No EPI | VX-710 | VX-853 | No EPI |
| 1 | 1 | 0.5 | 1 | 4 | 2 | 2 | 1 |
| 2 | 1 | 0.5 | 1 | 4 | 1 | 2 | 4 |
| 3 | 64 | 32 | 64 | 128 | 64 | 128 | >256 |
| 4 | 64 | 32 | 64 | 128 | 64 | 128 | 1 |
| 5 | 32 | 32 | 64 | 64 | 64 | 64 | 2 |
| 6 | 1 | 0.5 | 1 | 2 | 1 | 8 | 2 |
| 7 | 1 | 0.5 | 1 | 2 | 1 | 2 | 1 |
| 8 | 64 | 32 | 32 | 128 | 64 | 128 | 128 |
| 9 | 1 | 1 | 1 | 4 | 2 | 2 | 1 |
| 10 | 32 | 16 | 64 | 64 | 32 | 64 | 2 |
| 11 | 32 | 16 | 32 | 128 | 64 | 64 | 16 |
| 12 | 0.5 | 0.5 | 1 | 2 | 1 | 2 | 4 |
| 13 | 1 | 0.5 | 0.5 | 2 | 1 | 2 | 2 |
| 14 | 0.5 | 0.25 | 0.5 | 4 | 0.5 | 2 | 1 |
| 15 | 2 | 1 | 2 | 4 | 2 | 4 | 4 |
| 16 | 1 | 1 | 1 | 4 | 2 | 4 | 0.5 |
| 17 | 1 | 0.5 | 1 | 4 | 2 | 2 | 4 |
| 18 | 64 | 32 | 64 | 128 | 64 | 128 | >256 |
| 19 | 1 | 1 | 1 | 4 | 2 | 4 | 2 |
| 20 | 1 | 0.5 | 1 | 4 | 2 | 2 | 2 |
| 21 | 0.5 | 0.5 | 1 | 2 | 1 | 4 | 1 |
| 22 | 64 | 32 | 64 | 128 | 64 | 128 | 1 |
| 23 | 64 | 32 | 32 | 64 | 32 | 64 | 2 |
| 24 | 32 | 16 | 32 | >256 | 32 | 64 | 1 |
| 25 | >64 | 32 | 64 | 128 | 64 | 128 | 1 |
| 26 | 64 | 32 | 64 | >256 | 64 | 128 | >256 |

[a]MIC shows methicillin-resistant or -susceptible phenotype (methicillin breakpoint ≧4 µg/ml);
[b]EPIs were used at 50 µg/ml.
[c]MIC shows vancomycin-resistant or -susceptible phenotype (vancomycin breakpoint ≧32 µg/ml).

What is claimed is:

1. A pharmaceutical composition comprising:
   (i) an antibiotic selected from EtBr, ciprofloxacin, norfloxacin, gentamicin, or tetraphenyl-phosphonium bromide; and
   (ii) the compound:

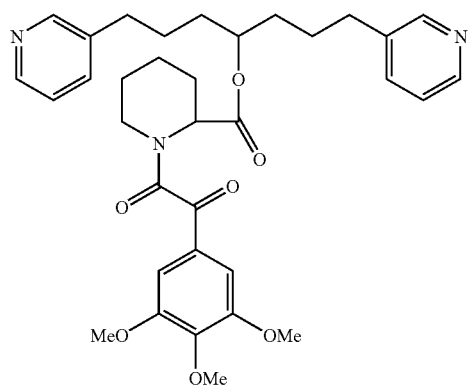

or a pharmaceutically acceptable salt thereof.

2. The composition according to claim 1, wherein said antibiotic is selected from ciprofloxacin, norfloxacin, or gentamicin.

3. The composition according to claim 1, wherein said antibiotic is ciprofloxacin.

4. The composition according to claim 1, wherein said antibiotic is EtBr.

5. The composition according to claim 1, wherein said antibiotic is tetraphenyl-phosphonium bromide.

* * * * *